(12) United States Patent
Wang et al.

(10) Patent No.: US 7,524,821 B2
(45) Date of Patent: Apr. 28, 2009

(54) SCAFFOLDED MALEIMIDE CLUSTERS FOR MULTIVALENT PEPTIDE ASSEMBLY

(75) Inventors: Lai-Xi Wang, Ellicott City, MD (US); Jiahong Ni, Baltimore, MD (US); Hengguang Li, Baltimore, MD (US); Suddham Singh, Durham (GB)

(73) Assignee: University of Maryland Biotechnology Institute, Baltimore, MD (US)

( * ) Notice: Subject to any disclaimer, the term of this patent is extended or adjusted under 35 U.S.C. 154(b) by 368 days.

(21) Appl. No.: 10/518,108

(22) PCT Filed: Jun. 20, 2003

(86) PCT No.: PCT/US03/19779

§ 371 (c)(1), (2), (4) Date: Dec. 10, 2004

(87) PCT Pub. No.: WO04/000802

PCT Pub. Date: Dec. 31, 2003

(65) Prior Publication Data

US 2005/0159341 A1   Jul. 21, 2005

Related U.S. Application Data

(60) Provisional application No. 60/390,776, filed on Jun. 20, 2002.

(51) Int. Cl.
*A61K 31/70* (2006.01)
*A01N 43/04* (2006.01)

(52) U.S. Cl. .................... 514/25; 514/2; 514/23

(58) Field of Classification Search .................... None
See application file for complete search history.

(56) References Cited

OTHER PUBLICATIONS

Garnett Advanced Drug Delivery Reviews (2001), vol. 53, pp. 171-216.*

Akerfeldt, K. S., R. M. Kim, D. Camac, J. T. Groves, J. D. Lear, and W. F. DeGrado. 1992. Tetraphilin: a four-helix proton channel built on a tetraphenylporphyrin framework. J. Am. Chem. Soc. 114:9656-9657.

Blaskovich, M. A., Q. Lin, F. L. Delarue, J. Sun, H. S. Park, D. Coppola, A. D. Hamilton, and S. M. Sebti. 2000. Design of GFB-111, a platelet-derived growth factor binding molecule with antiangiogenic and anticancer activity against human tumors in mice. Nat. Biotechnol. 18: 1065-70.

Brask, J., and K. J. Jensen. 2000. Carbopeptides: chemoselective ligation of peptide aldehydes to an aminooxy-functionalized D-galactose template. J. Pept. Sci. 6:290-9.

Brask, J., and K. J. Jensen. 2001. Carboproteins: a 4-alpha-helix bundle protein model assembled on a D-galactopyranoside template, Bioorg. Med. Chem. Lett. 11:697-700.

Calvo-Calle, J. M., G. A. de Oliveira, P. Clavijo, M. Maracic, J. P. Tam, Y. A. Lu, E. H. Nardin, R. S. Nussenzweig, and A. H. Cochrane. 1993. Immunogenicity of multiple antigen peptides containing B and non-repeat T cell epitopes of the circumsporozite protein of *Plasmodium falciparum*, J. Immunol. 150:1403-12.

Chan, D. C., and P. S. Kim. 1998. HIV entry and its inhibition. Cell. 93:681-4.

Dubber, M., and T. K. Lindhorst. 1998. Synthesis of octopus glycosides: core molecules for the construction of glycoclusters and carbohydrate-centered dendrimers. Carbohydr. Res. 310:35-41.

Guan, Q.; Li, C.; Schmidt, E. J.; Boswell, J. S.; Walsh, J. P.; Allman, G. W.; Savage, P. B. 2000. Preparation and Characterization of Cholic Acid-Derived Antimicrobial Agents with Controlled Stabilities. Org. Lett. 2:2837-2840.

(Continued)

*Primary Examiner*—Patrick T Lewis
(74) *Attorney, Agent, or Firm*—Marianne Fuierer; Deborah H. Spencer; Moore & Van Allen PLLC

(57) ABSTRACT

Disclosed are scaffolded maleimide clusters, methods of making said clusters and use of said clusters as templates for multivalent peptide assembly. Multiple maleimide functionalities were introduced onto a scaffold molecule by the reaction of a core-centered polyamines with methoxycarbonyl-maleimide or with activated esters of maleimide-containing compounds. The scaffolded maleimides allow rapid, highly chemoselective, and high-yield ligation with thiolcontaining peptides under virtually neutral conditions at room temperature. The disclosed mild and highly efficient ligation method is extremely valuable for synthesizing large and complex multivalent peptides that may not be easily obtained by conventional ligation methods. These novel scaffolded maleimide clusters allow a highly chemoselective ligation with a thiolcontaining peptide under virtually neutral conditions, providing a new and efficient approach for multivalent peptide assembly. The disclosed mild and highly efficient ligation method is extremely valuable for synthesizing large and complex multivalent peptides that may not be easily obtained by conventional ligation methods. A series of multivalent peptides containing the sequence of the 36-mer HIV-1 inhibitor DP178 (T20), the T-helper epitope from tetanus toxoid (830-844), and the minimum epitope sequence of the potent HIV-neutralizing antibody 2F5 were synthesized. Carbohydrates and cholic acid were chosen as the scaffold because of their rigidity and mufti-functionality. Thus, the topology of the multivalent peptides can be controlled by the defined spatial orientation of the maleimide functionalities on the rigid scaffold core. The resulting multivalent gp41 peptides incorporating strands of DP178 on the monosaccharide and the cholic acid templates were found to be able to form three or four a-helix bundles. Moreover, the multivalent peptides containing strands of the long gp41 peptide DP178 were highly immunogenic and were able to raise high titers of peptide-specific antibodies in the absence of any additional adjuvant. Therefore, these and related multivalent peptides constructed on the maleimide clusters may be used as novel immunogens, potential inhibitors, protein mimics, artificial proteins, and powerful antigens for a broad range of biomedical applications.

10 Claims, 13 Drawing Sheets

OTHER PUBLICATIONS

Jensen, K. J., and G. Barany. 2000. carbopeptides:carbohydrates as potential templates for de novo design of protein models. J. Pept. Res. 56:3-11.

Kilby, J. M., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag. 1998. Potent suppression of HIV-1 replication in humans by T-20, a peptide inhibitor of gp41-mediated virus entry. Nat. Med. 4: 1302-7.

Lawless, M. K., S. Barney, K. I. Guthrie, T. B. Bucy, S. R. Petteway, Jr., and G. Merutka. 1996. HIV-1 membrane fusion mechanism: structural studies of the interactions between biologically-active peptides from gp41. Biochemistry. 35: 13697-708.

Leydet, A.; C. Jeantet-Segonds, C. Bouchitte, C. Moullet, B. Boyer, J. P. Roque, M. Witvrouw, J. Este, R. Snoeck, G. Andrei, and E. De Clercq. 1997. Polyanion inhibitors of human immunodeficiency virus and other viruses. 6. Micelle-like anti-HIV polyanionic compounds based on a carbohydrate core. J. Med. Chem. 40:350-6.

Lin, Q., H. S. Park, Y. Hamuro, C. S. Lee, and A. D. Hamilton. 1998. Protein surface recognition by synthetic agents: design and structural requirements of a family or artificial receptors that bind to cytochrome c. Biopolymers. 47:285-97.

Lindhorst, T. K. 2002. Artificial multivalent sugar ligands to understand and manipulate carbohydrate-protein interactions. Top. Curr. Chem. 218:201-235.

Lu, Y. A., P. Clavijo, M. Galantino, Z. Y.Shen, W. Liu, and J. P. Tam. 1991. Chemically unambiguous peptide immunogen: preparation, orientation and antigenicity of purified peptide conjugated to the multiple antigen peptide system. Mol. Immunol. 28:623-30.

Lyu, P. C.; Sherman, J. C.; Chen, A.; Kallenbach, N. R. 1991. α-Helix stabilization by natural and unnatural amino acids with alkyl side chains. Proc. Natl. Acad. Sci. USA. 88:5317-5320.

Madder, A.; Li, L.; De Muynck, H.; Farcy, N.; Van Haver, D.; Fant, F.; Vanhoenacker, G.; Sandra, P.; Davis, A. P.; De Clercq, P. J. 2002. Evaluation of a Two-Stage Screening Procedure in the Combinatorial Search for Serine Protease-Like Activity. J. Comb. Chem. 4:552-562.

Malashkevich, V. N., D. C. Chan, C.T. Chutkowski, and P. S. Kim. 1998. Crystal structure of the simian immunodeficiency virus (SIV) gp41 core: conserved helical interactions underlie the broad inhibitory activity of gp41 peptides. Proc. Natl. Acad. Sci. USA. 95:9134-9.

McGeary, R. P., I. Jablonkai, and I. Toth. 2001. Carbohydrate-based templates for synthetic vaccines and drug delivery. Tetrahedron. 57:8733-8742.

Muster, T., F. Steindl, M. Purtscher, A. Trkola, A. Klima, G. Himmler, F. Ruker, and H. Katinger. 1993. A conserved neutralizing epitope on gp41 of human immunodeficiency virus type I. J. Virol. 67:6642-7.

Mutter, M., and G. Tuchscherer. 1997. Non-native architectures in protein design and mimicry. Cell Mol. Life Sci. 53:851-63.

Mutter, M., G. G. Tuchscherer, C. Miller, K. H. Altmann, R. I. Carey, D. F. Wyss, A. M. Labhardt, and J. E. Rivier. 1992. Template-assembled synthetic proteins with four-helix-bundle topolgy. Total chemical synthesis and conformational studies. J. Am. Chem. Soc. 114: 1463-1470.

Nardelli, B., Y. A. Lu, D. R. Shiu, C. Delpierre-Defoort, A. T. Profy, and J. P. Tam. 1992. A chemically defined synthetic vaccine model for HIV-1. J. Immunol. 148:914-20.

Nefzi, A.; Sun, X.; Mutter, M. 1995. Chemoselective ligation of multifunctional peptides to topological templates via thioether formation for TASP synthesis. Tetrahedron Lett. 36:229-230.

Ni, J.H., S. Singh, and L. X. Wang. 2002. Improved preparation of perallylated cyclodextrins: facile synthesis of cyclodextrin-based polycationic and polyanionic compounds. Carbohydr Res. 337:217-20.

Park, H. S., Q. Lin, and A. D. Hamilton. 1999. Protein surface recognition by synthetic receptors: a route to novel submicromolar inhibitors for alpha-chymotrypsin. J. Am. Chem. Sot. 121:8-13.

Peczuh, M. W., and A. D. Hamilton. 2000. Peptide and protein recognition by designed molecules. Chem. Rev. 100:2479-2494.

Rose, K. 1994. Facile synthesis of homogeneous artificial proteins. J. Am. Chem. Soc. 116:30-33.

Sasaki, T., and E. T. Kaiser. 1989. Helichrome: Synthesis and enzymatic activity of a designed hemeprotein. J. Am. Chem. Soc. 111:380-381.

Shao, J., and J. P. Tam. 1995. Unprotected peptides as building blocks for the synthesis of peptide dendrimers with oxime, hydrazone, and thiazolidine linkages. J. Am. Chem. Soc. 117:3893-3899.

Tam, J. P. 1996. Recent advances in multiple antigen peptides. J. Immunol. Methods. 196:17-32.

Tam, J. P. 1988. Synthetic peptide vaccine design: synthesis and properties of a high-density multiple antigenic peptide system. Proc. Natl. Acad. Sci. USA. 85:5409-13.

Tam, J. P., and Y. A. Lu. 1989. Vaccine engineering: enhancement of immunogenicity of synthetic peptide vaccines related to hepatitis in chemically defined models consisting of T- and B-cell epitopes. Proc. Natl. Acad. Sci. USA. 86:9084-8.

Tam, J. P., Y. A. Lu, and J. L. Yang. 2002. Antimicrobial dendrimeric peptides. Eur. J. Biochem. 269:923-932.

Tuchscherer, G. 1993. Template assembled synthetic proteins: condensation of a multifunctional peptide to a topological template via chemoselective ligation. Tetrahedron Lett. 34:8419-8422.

Tuchscherer, G., D. Grell, M. Mathieu, and M. Mutter. 1999. Extending the concept of template-assembled synthetic proteins. J. Pept. Res. 54: 185-94.

Tuchscherer, G., C. Servis, G. Corradin, U. Blum, J. Rivier, and M. Mutter. 1992. Total chemical synthesis, characterization, and immunological properties of an MHC class I model using the TASP concept for protein de novo design. Protein Sci. 1: 1377-86.

Wang, C. Y., D. J. Looney, M. L. Li, A. M. Walfield, B. Hosein, J. Ye, J. P. Tam, and F. Wong-Staal. 1991. Long-term high-titer neutralizing activity induced by octameric synthetic HIV-1 antigen. Science. 254-285-8.

Wild, C. T., D. C. Shugars, T. K. Greenwell, C. B. McDanal, and T. J. Matthews. 1994. Peptides corresponding to a predictive alpha-helical domain of human immunodeficiency virus type I gp41 are potent inhibitors of virus infection. Proc. Natl. Acad. Sci. USA. 91:9770-4.

Zhou, X-T.; Atiq-ur Rehman; Li, C.; Savage, P. B. 2000. Preparation of a Protected Triamino Analogue of Cholic Acid and Sequential Incorporation of Amino Acids in Solution and on a Solid Support. Org. Lett. 2:3015-3018.

* cited by examiner

Ac-YTSLIHSLIEESQNQQEKNEQELLELDKWASLWNWFC-NH$_2$
14 (P37C)

R = spacer with the length of 1-50 atoms, where the atoms could be C, N, O, P, S and any other possible atoms and their combinations.

X = any functional groups or moieties, such as peptides, proteins, lipids, carbohydrates, and nucleic acids, or simple functional groups such as OH, NH2, etc.

P-7C: Ac-Glu-Leu-Asp-Lys-Trp-Ala-Cys-NH$_2$
P-37C: Ac-YTSLIHSLIEESQNQQEKNEQELLELDKWASLWNWFC-NH$_2$
T-helper: CGSSSQYIKANSKFIGITEL-NH$_2$ ary peptide assembly (Blaskovich et al., 2000; Lin et al., 1998; Park et al., 1999; Tam et al, 2002). In addition to an oligo-lysine core, (Tam, 1996) other types of templates that were developed for multivalent peptide construction include cyclic peptide and derivatives (Mutter et al., 1992; Tuchscherer, 1993; Tuchscherer et al., 1992; Nefzi, et al., 1995), porphyrin molecules (Akerfeldt et al., 1992; Sasaki et al., 1989), calix [4] arene core (Blaskovich et al., 2000; Lin et al., 1998; Park et al., 1999) and carbohydrates (Brask et al., 2000; Brask et al., 2001; Jensen et al., 2000; McGeary et al., 2001; Wang, et al, 2003). Although multivalent peptides may be assembled by a stepwise solid phase peptide synthesis on an immobilized template, the solid phase synthesis itself and the purification of the high molecular weight multivalent peptide product to real homogeneity, after cleavage and deprotection, present a clear challenge (Tam, 1988). The recent development of techniques in chemoselective ligation of pre-assembled, unprotected peptide segments has significantly enhanced our ability to synthesize large, complex multivalent peptides and proteins (Mutter, 1997; Tam, 1996; Tuchscherer et al., 1999). Since polypeptides usually contain a batch of functional groups (e.g., carboxyl, amino, and hydroxyl groups, as well as aromatic side chains), the success of the ligation approach relies on a highly chemoselective reaction between a pair of mutually reactive functionalities that are placed on the unprotected peptide and the scaffold, respectively, which should not react crossly with any other functional groups in the polypeptides. Toward this end, two chemoselective reactions are most commonly used for multivalent peptide synthesis. One is the reaction of aminooxy or hydrazone nucleophiles with aldehydes/ketones, which results in the formation of oximes and hydrazones, respectively (Brask et al., 2000; Rose, 1994; Shao et al., 1995; Tuchscherer, 1993). The reaction is performed under acidic conditions (pH 4-5), and the oximes or hydrazones formed are chemically stable under acidic to neutral conditions. However, this ligation is usually not applicable for peptides that are not soluble under acidic conditions such as a series of gp41 C-peptides. The other commonly used chemoselective reaction is the thioether formation between thiol groups (usually from cysteine residues) and bromoacetyl or chloroacetyl moieties through nucleophilic substitution (Lu et al., 1991; Robey et al., 1989). However, an efficient nucleophilic substitution between a thiol-chloroacetyl (or bromoacetyl) reactive pair can efficiently take place only under basic conditions (pH 8-9), and side reactions between free amino groups in the polypeptides and the haloacetyl groups may occur under the reaction conditions (Robey et al., 1989). The limitations and disadvantages of the currently available chemoselective ligation methods have prompted the invention of highly efficient, generally applicable methods for multivalent peptide assembling. This instant invention discloses the preparation of structurally defined scaffolded maleimide clusters and their application for the construction of various multivalent peptides for a range of applications.

One area for the use of multivalent peptides is HIV vaccines and viral membrane fusion inhibitors. The HIV-1 gp41 is an envelope glycoprotein that mediates the fusion of viral and cellular membranes, a critical step for HIV entry and infection. It was reported that synthetic gp41 C-peptides (peptides corresponding to the C-terminal ectodomain of gp41) such as T20 and C34, potently inhibit membrane fusion by both laboratory-adapted strains and primary isolates of HIV-1 (Malashkevich et al., 1998; Wild et al., 1993; Wild et al., 1994). The critical roles of certain peptide domains of gp41 in mediating membrane fusion provide ideal targets for developing therapeutic and preventative agents against HIV/AIDS (Chan et al., 1998). The invention allowed the construction of various multivalent gp41 peptides as mimics of the fusion-active states of oligomeric gp41 expressed on HIV-1, which may be used as effective HIV-1 vaccine and inhibitors.

Another area for the use of the multivalent peptides constructed from the maleimide clusters is for artificial protein design. The maleimide clusters assembled on a rigid scaffold molecule such as monosaccharides and cholic acid can well control the topology of the peptide strands ligated onto the templates, leading to the formation of secondary structure such as α-helix bundles.

BRIEF SUMMARY OF THE INVENTION

Disclosed are carbohydrate-centered maleimide clusters, cholic acid-based maleimide clusters, and other related maleimide clusters and the facile synthesis thereof. These maleimide clusters take advantage of the well-established, highly efficient Michael-type addition of a thiol group to a maleimide moiety (Kitagawa et al., 1976; Peeters et al., 1989). The instant scaffolded maleimide clusters allow a highly chemoselective ligation with a thiol-containing peptide under virtually neutral conditions, providing a new and efficient approach for multivalent peptide assembly. The disclosed mild and highly efficient ligation method is extremely advantageous for synthesizing large and complex multivalent peptides that may not be easily obtained by conventional ligation methods. A series of multivalent peptides containing the sequence of the 36-mer HIV-1 inhibitor DP178 (T20), the T-helper epitope from tetanus toxoid (830-844), and the minimum epitope sequence of the potent HIV-neutralizing antibody 2F5 were synthesized.

We chose carbohydrates and cholic acid as the scaffold because the rigid ring structure and the distinct configurations of multiple functionalities in the scaffold make them unique platforms for topological accommodations of peptide chains. Thus, the topology of the multivalent peptides can be controlled by the defined spatial orientation of the maleimide functionalities on the rigid scaffold core. The resulting multivalent gp41 peptides incorporating strands of DP178 on the monosaccharide and the cholic acid templates were found to be able to form three or four α-helix bundles. Moreover, the multivalent peptides containing strands of the long gp41 peptide DP178 were highly immunogenic and were able to raise high titers of peptide-specific antibodies, in the absence of any additional adjuvant. Therefore, these and related multivalent peptides constructed on the maleimide clusters may be used as novel immunogens, potential inhibitors, protein mimics, artificial proteins, and powerful antigens for a broad range of biomedical applications.

DETAILED DESCRIPTION OF THE INVENTION

Figure 1:
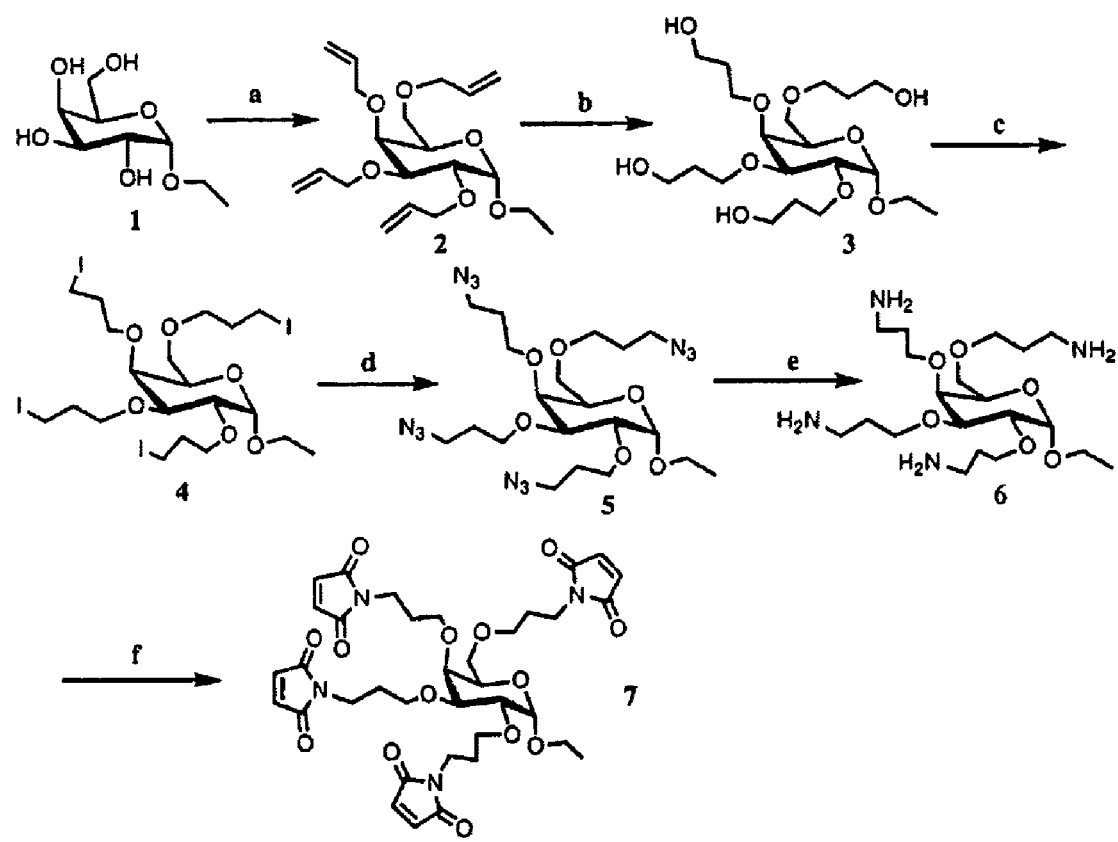
FIG. 1. Synthesis of a galactoside-based, tetravalent maleimide cluster. (a) allyl bromide, NaH/DMF, 0° C.-room temp., 94%; (b) 9-BBN, THF, reflux, then 3 M aqueous. NaOH, 30% $H_2O_2$, 0° C.-room temp., 84%; (c) $PPh_3/I_2$, DMF, 80° C., 70%; (d) $NaN_3$, DMF, room temp. 78%; (e) Pd/C, $H_2$, MeOH, room temp., 100%; (f) methoxycarbonylmaleimide, 1 M aqueous $NaHCO_3$, MeCN, room temp., 76%.

As used herein, a multivalent peptide is a compound comprising more than one peptide covalently attached to a scaffold compound. A peptide comprises two or more amino acids covalently linked by a peptide bond. Any peptide that contains a cysteine residue is able to react with a maleimide moiety and form a covalent bond. A scaffold compound is defined herein as a core compound comprising two or more reactive groups whereby a peptide can be covalently attached. For the instant invention, scaffolds can be, but are not limited to monosaccharides, polyols and oligosaccharides. Monosaccharides that can serve as a scaffold of the instant invention include but are not limited to dihydroxyacetone, R and L enantiomeric and anomeric forms of glyceraldehyde, threose, erythrose, erythrulose, ribose, arabinose, xylose, lyxose, ribulose, xylulolse, allose, altrose, glucose, mannose, gulose, idose, galactose, talose, psicose, fructose, sorbose and tagatose. Polyols or polyalchohols that can serve as a scaffold compound include, but are not limited to, glyceritol, threitol, erythritol, ribitol, arabinitol, xylitol, lyxitol, allitol, altritol, glucitol, mannitol, galactitol, talitol, gulitol, iditol, sorbitol, mannitol, glycerol, inositol, maltitol, lactitol, dulcitol and adonitol. Oligosaccharides that can serve as a scaffold compound include, but are not limited to, disaccharides comprising any combination of monosaccharides described supra and cyclic oligosaccharides comprising the monosaccharides described supra. Cyclodextrin and cyclofructin are examples of cyclic oligosaccharides that can be used in the scaffold of the instant invention. Cyclodextrins are cyclic (α-1, 4)-linked oligosaccharides and include, but are not limited to 5-13 α-D-gluco-pyranose, cyclomannin, cycloaltrin and cyclogalactin. Cyclodextrins comprise a hydrophobic core, capable of carrying compounds. A maleimide cluster may further comprise several linked core compounds comprising reactive maleimide moieties. A core molecule for the instant invention also includes, but is not limited to, cholic acid, cholesterol, cyclic peptides, porphyrins and calyx [4] arene, carbohydrates and polyamines. Polyamines include, but are not limited to, bis aminopropyl piperazine, iminobis propylamnine, methylimino bis propylamine, diamine propane, biamino butane, putrescine, cadaverine, spermidine and polyamines produced by the allylation and subsequent photoaddition of oligosaccharides. Essentially any compound containing a reactive group whereby a maleimide linker arm can be attached is a suitable core molecule for the instant invention.

For the scaffold of the instant invention, the reactive groups are maleimides that form covalent bonds with peptides containing a reactive thiol group, such as a cysteine residue. As used herein, a maleimide cluster is defined as a scaffold comprising more than one maleimide.

The reactive groups of a scaffold are attached either directly to a core compound or via linkers. The linkers are of various lengths and comprise any combination of C, N, O, P and S atoms as the backbone of the linker. These linkers between the core compound and the reactive group may be 1-50 atoms in length. Such atoms include, but are not limited to, carbon, nitrogen, oxygen, phosphorous and sulfur. The linkers are preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 atoms in length.

As defined herein, multivalent peptides are a maleimide cluster with covalently attached peptides. The peptides of a multivalent peptide are either the same or different. The instant disclosure further describes compositions comprising multivalent peptides and maleimide clusters. A composition may comprise multivalent peptides where the peptides are identical, not identical or a combination of identical and non-identical peptides. Additionally, the scaffolded clusters of the instant invention may comprise not only maleimide but also maleimide and other thiol-reactive compounds.

Pharmaceutical compositions include multivalent peptides and/or maleimide clusters with a pharmaceutically acceptable carriers. Pharmaceutically acceptable carriers includes those approved for use in animals and humans and include diluents, adjuvants, excipients or any vehicle with which a compound, such as multivalent peptides and/or maleimide clusters, is administered. Pharmaceutically acceptable carriers include but are not limited to water, Ringer's solution, isotonic saline, oils, dextrose solutions, glycerol solutions, excipients such as starch, glucose, lactose, sucrose, gelatin, malt, rice, flour, chalk, silica gel, sodium stearate, glycerol monostearate, talc, sodium chloride, powdered non-fat milk, propylene glycol and ethanol. Pharmaceutical compositions may also include wetting or emulsifying agents, or pH buffering compounds. Wetting or emulsifying agents include, but are not limited to, sodium dodecyl sulfate, polyoxyethylene derivatives of fatty acids, partial esters of sorbitol anhydrides, TWEEN 80, TWEEN 20, POLYSORBATE 80, TRITON X 100, bile salts such as sodium deoxycholate, zwitterionic detergents such as N-dodecyl-N,N-dimethyl-2-ammonio-1 ethane sulphonate and its congeners or non-ionic detergents such as octyl-beta-D-glucopyranoside.

The multivalent peptides can be formulated into a composition in a neutral or salt form. Pharmaceutically acceptable salts, include the acid addition salts (formed with the free amino groups of the peptide) and which are formed with inorganic acids include, but are not limited to, hydrochloric or phosphoric acids, or such organic acids as acetic, oxalic, tartaric and mandelic. Salts formed with the free carboxyl groups can also be derived from inorganic bases which include, but are not limited to, sodium, potassium, ammonium, calcium, or ferric hydroxides, and such organic bases as isopropylamine, trimethylamine, histidine and procaine.

Adjuvants include but are not limited to alum, mineral oil, cholera toxin b-subunit, dehydroepiandrosterone sulfate, Freund's (complete and incomplete), lysolecithin, pluronic polyols, keyhole limpet hemocyanin, dinitrophenol, *Bacillus* Calmette-Guerin and *Corynebacterium parvum*.

Pharmaceutically acceptable buffers are known in the art and include but are not limited to sodium phosphate, sodium citrate, sodium acetate, TRIS glycine, HEPES, MOPS or Bis-Tris.

The multivalent peptides of the instant invention are useful in many different ways. A multivalent peptide allows the delivery of peptides for vaccination. Compaction of DNA by polycations in conjunction with the multivalent peptide allows delivery of DNA into cells. Such multivalent peptides may also comprise peptides which would guide the import and localization into cells, and can be used to deliver drugs in addition to DNA. Protein folding can be studied using the maleimide cluster scaffold. Peptides attached to the maleimide cluster scaffold exhibit an increased percentage of peptides having helical structure, allowing the study of protein folding. Additionally, increased antigenicity is obtained for the multivalent peptides, possibly due to an increased percentage of the attached peptides having an ordered folded structure.

Enzymes may be immobilized on the maleimide cluster. Such immobilized enzymes may provide for improved stability of the enzymes. Enzymes of a pathway may be placed in proximity to each other using a maleimide cluster, improving overall activity of the enzymatic pathway by reducing substrate diffusion and providing for channeling of the substrate between the enzymes.

Any compound containing a thiol group can be attached to the maleimide clusters of the instant invention. For peptides and proteins that do not have an available reactive thiol, various methods of adding cysteine to any amino acid sequence are well known in the art. For non-peptide and non-protein compounds, various methods of thiol addition to non-peptide and non-protein compounds are also well known in the art.

Attachment of peptides and proteins to the scaffolded maleimide clusters of the instant invention increases valency of the peptide(s) or protein(s). With the attachment of the peptide or protein to the scaffold, the stability of the peptide or protein is increased. Such stability is observed in native or more native conformation of the peptide or protein when attached to the scaffold of the instant invention. Furthermore, with the multivalency of the scaffold, adjuvants may be attached to the same scaffold along with antigens.

In addition to maleimide, other possible thiol reactive compounds are iodoacetic acid, bromoacetic acid, iodoacetamide and pyridyl disulfide. The disulfide linkages formed with pyridyl disulfide are cleavable by methods well known in the art. Any number of thiol reactive groups may be added to a core molecule or core molecules, including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49 and 50 thiol reactive groups.

Furthermore, multivalent peptides comprising a maleimide cluster can be used either orally or parenterally, wherein parentally as used herein refers to modes of administration which include intravenous, intramuscular, intraperitoneal, instrasternal, subcutaneous and intraarticular injection and infusion.

Suitable proteins for attachment to the scaffolded maleimide cluster of the instant invention include, but are not limited to, toleragens, vaccine peptides and proteins, receptors and mimics, ligands and mimics, toxins, transition-states analogues of multiple protein-protein interactions, T-helper cell and B-cell epitopes, and CTL epitopes. Suitable proteins include, but are not limited to CD4, CD5, CD8, CCR5, CCR4, CCR3, CCR1, HIV-I Tat, gp41, gp120, MHC I and MHC II proteins, IL-1, IL-2, IL-4, IL-10.

A preferred embodiment of the instant invention is a maleimide cluster comprising a core molecule wherein five or more maleimides are each attached to the core. Another preferred embodiment of the invention is a maleimide cluster comprising a carbohydrate core wherein two or more maleimides are each attached to the core. Yet another preferred embodiment of the invention is a maleimide cluster comprising a core molecule wherein five or more maleimides are each attached to the core by a linker. Still another preferred embodiment of the invention is a maleimide cluster comprising a carbohydrate core wherein one, two, three, four, five or more maleimides are each attached to the core by a linker.

A preferred embodiment of the invention is a maleimide cluster comprising a cholic acid core wherein one, two, three, four, five or more maleimides are each attached to the core. Another preferred embodiment of the invention is a maleimide cluster comprising a cholic acid core wherein one, two, three, four, five or more maleimides are each attached to the core by a linker.

A further preferred embodiment of the invention is a maleimide cluster comprising a core molecule, wherein six or more maleimides are each attached to the core. Yet another preferred embodiment of the invention is a maleimide cluster comprising a core molecule, wherein seven or more maleimides are each attached to the core.

A preferred embodiment of the invention is a maleimide cluster comprising a core molecule wherein two or more maleimides are each attached to the core and wherein the core is selected from the group consisting of monosaccharides, polyols, oligosaccharides, cyclic oligosaccharides, polyamines, cholic acid, cholesterol, cyclic peptides, porphyrins and calyx [4] arene. A further preferred embodiment of the invention is a maleimide cluster comprising a core molecule wherein two or more maleimides are each attached to the core and wherein the core is a monosaccharide. Another further preferred embodiment of the invention is a maleimide cluster comprising a core molecule wherein two or more maleimides are each attached to the core and wherein the core is a polyol. Still another further preferred embodiment of the invention is a maleimide cluster comprising a core molecule wherein two or more maleimides are each attached to the core and wherein the core is an oligosaccharide. Yet another further preferred embodiment of the invention is a maleimide cluster comprising a core molecule wherein two or more maleimides are each attached to the core and wherein the core is a cyclic oligosaccharide. Another further preferred embodiment of the invention is a maleimide cluster comprising a core molecule wherein two or more maleimides are each attached to the core and wherein the core is a cholic acid.

A preferred embodiment of the invention is a maleimide cluster comprising cyclodextrin wherein one or more maleimides are each attached to the cyclodextrin by a linker. A preferred embodiment of the invention is a maleimide cluster comprising at least two cores wherein each core contains one or more maleimides. Another preferred embodiment of the invention is a maleimide cluster comprising a polyol core, wherein one or more maleimides are each attached to the core. A further preferred embodiment of the invention is a maleimide cluster comprising a polyol core, wherein two or more maleimides are each attached to the core by a linker.

A further preferred embodiment of the invention is a multivalent peptide or protein comprising said maleimide clusters described supra with peptides or proteins covalently attached to the maleimide. Another further preferred embodiment is a multivalent peptide or protein comprising said maleimide clusters described supra with peptides or proteins covalently attached to the maleimide, wherein the covalently attached peptides or proteins are identical in their amino acid sequence. Still another preferred embodiment is a multivalent peptide or protein comprising said maleimide clusters described supra with peptides or proteins covalently attached to the maleimide, wherein the covalently attached peptides or proteins differ in their amino acid sequence and there are two or more different peptides or proteins.

A preferred embodiment of the invention is a method of vaccination comprising administering a multivalent peptide or protein in an amount sufficient to elicit a protective immune response in an animal, wherein the multivalent peptide or protein comprises peptides or proteins covalently attached to said maleimide clusters, described supra. A further preferred embodiment of the invention is a method of vaccination comprising administering a multivalent peptide or protein in an amount sufficient to elicit a protective immune response in an animal, wherein the multivalent peptide or protein comprises peptides or proteins covalently attached to said maleimide clusters, described supra, wherein the covalently attached peptides or proteins are identical in their amino acid sequence. Another further preferred embodiment of the invention is a method of vaccination comprising administering a multivalent peptide or protein in an amount sufficient to elicit a protective immune response in an animal, wherein the multivalent peptide or protein comprises peptides or proteins covalently attached to said maleimide clusters, described supra, wherein the covalently attached peptides or proteins differ in their amino acid sequence and there are two or more different peptides or proteins.

A method of delivering a peptide drug comprising administering a multivalent peptide or protein containing a therapeutically effective amount of the peptide or protein drug to a patient in need thereof, wherein the multivalent peptide or protein comprises peptides or proteins covalently attached to said maleimide cluster s described supra. Another preferred embodiment is a method of delivering a peptide drug comprising administering a multivalent peptide or protein containing a therapeutically effective amount of the peptide or protein drug to a patient in need thereof, wherein the multivalent peptide or protein comprises peptides or proteins covalently attached to said maleimide clusters, described supra, wherein the covalently attached peptides or proteins are identical in their amino acid sequence. Still another preferred embodiment of the invention is a method of delivering a peptide drug comprising administering a multivalent peptide or protein containing a therapeutically effective amount of the peptide or protein drug to a patient in need thereof, wherein the multivalent peptide or protein comprises peptides or proteins covalently attached to said maleimide clusters, described supra, wherein the covalently attached peptides or proteins differ in their amino acid sequence and there are two or more different peptides or proteins.

A preferred embodiment of the invention is a method of making a multivalent peptide or protein comprising contacting peptides or proteins containing a thiol group with said maleimide cluster, described supra. A further preferred embodiment of the invention is a method of making a multivalent peptide or protein comprising contacting peptides or proteins containing a thiol group with said maleimide cluster, described supra, wherein the peptides or proteins are identical in amino acid sequence. Another further preferred embodiment of the invention is a method of making a multivalent peptide or protein comprising contacting peptides or proteins containing a thiol group with said maleimide cluster, described supra, wherein the peptides or proteins differ in their amino acid sequence and there are two or more different peptides or proteins. Still another further preferred embodiment of the invention is a method of making a multivalent peptide or protein comprising contacting peptides or proteins containing a thiol group with said maleimide cluster, described supra, wherein the peptides or proteins are identical in amino acid sequence.

A preferred embodiment of the invention is a method of producing polyclonal antibodies to a peptide or protein comprising administering said peptide or protein covalently attached to said maleimide clusters, described supra, to an animal and isolating the polyclonal antibodies produced.

A preferred embodiment of the invention is a method of producing monoclonal antibodies to a peptide or protein comprising administering said peptide or protein covalently attached to said maleimide clusters, described supra, to an animal, isolating the spleen to produce hybridomas and isolating the monoclonal antibodies produced.

A preferred embodiment of the invention is a method for targeting specific cells or cellular organelles for delivery of a compound comprising said maleimide clusters, discussed supra, comprising an attached targeting protein.

A preferred embodiment of the invention is a method of making a multivalent peptide or protein comprising adding a cysteine to said peptide or protein and contacting with said maleimide clusters, discussed supra, to form a covalent bond. A preferred embodiment of the invention is a method of making a multivalent compound comprising covalently adding a thiol to a compound and contacting with said maleimide clusters, described supra, to form a covalent bond.

A preferred embodiment of the invention is a maleimide cluster comprising at least two cores wherein each core contains one, two, three, four, five or more maleimides. A preferred embodiment of the invention is a multivalent peptide comprising the maleimide cluster comprising a carbohydrate core or a cholic acid core or any other cores wherein three or more maleimides are each attached to the core by a linker with peptides covalently attached to the maleimides. A preferred embodiment of the invention is a multivalent peptide comprising a maleimide cluster comprising at least three cores wherein each core contains three or more maleimides with peptides covalently attached to the maleimides. Another preferred embodiment is a linker of the maleimide cluster comprising C, N, O, P or S atoms. A more preferred embodiment is where the linker is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 atoms in length and comprising any combination of C, N, O, P or S atoms.

EXAMPLE 1

A galactoside-based, tetravalent maleimide cluster (7) was synthesized through a series of efficient chemical transformations (FIG. 1). First, compound (1) was allylated with allyl bromide to give the tetra-O-allyl galactoside (2)(94%). The tetra-allyl derivative was then subject to regioselective hydroboration with 9-borabicyclo-[3.3.1]nonane (9-BBN) and subsequent alkaline oxidation with $H_2O_2$ to give the tetra-O-(3-hydroxypropyl) galactoside (3) in 84% yield. To synthesize the tetra-amino derivative (6) that is required for introducing maleimide groups, the tetraol (3) was reacted with triphenylphosphine-iodine in DMF to give the tetraiodide (4)(70%), which was then converted into the azido-compound (5) by treatment with $NaN_3$ in DMF. Catalytic hydrogenation of 5 afforded the tetra-amino derivative (6) in a quantitative yield. Finally, simultaneous introduction of 4 maleimide groups was achieved by treating the amine (6) with methoxycarbonylmaleimide in aqueous MeCN containing $NaHCO_3$ to give the tetravalent maleimide cluster (7) in 76% yield (FIG. 1).

EXAMPLE 2

Figure 2:
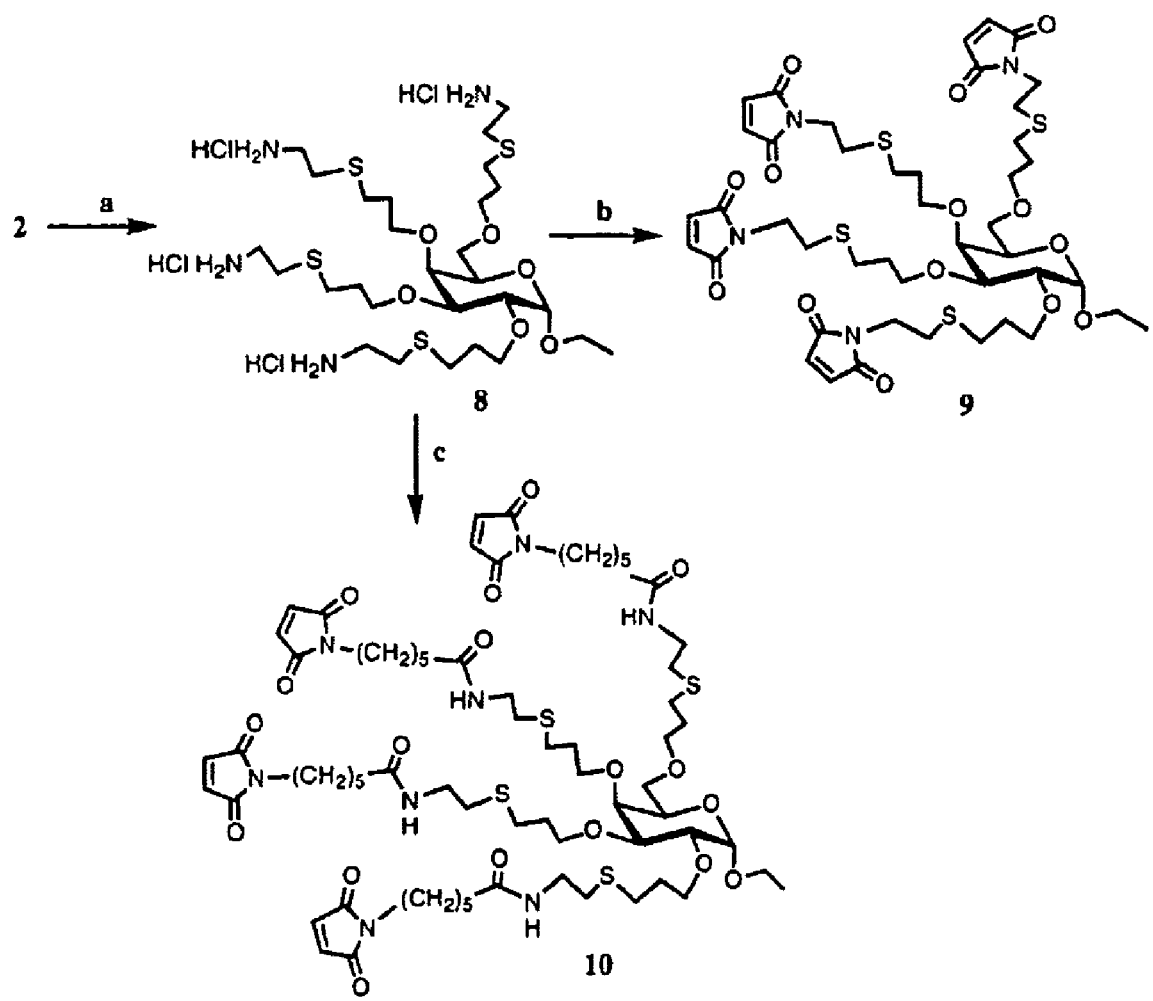
FIG. 2. Synthesis of a tetravalent maleimnide cluster with spacers between the carbohydrate core and the maleimide. (a) cysteamine hydrochloride, MeOH, hv, room temp., 80%; (b) methoxycarbonylmaleimide, 1 M aqueous $NaHCO_3$, MeCN, room temp., 71%; (c) 6-maleimidohexanoic acid N-succinimidyl ester, 1 M aqueous $NaHCO_3$, THF, 0° C.-room temp., 43%.

The synthesis of maleimide clusters with variable length of spacers between the carbohydrate core and the maleimide was easily achievable by extending the spacers during the synthesis. The length of spacers between the carbohydrate core and the peptide chains is an important factor to determine the orientation and intra-molecular interaction of the peptide chains, which will eventually affect the properties of the resulting multivalent peptides (Peczuh et al., 2000; Tam, 1996) For the purpose, two tetravalent maleimide clusters (compounds 9 and 10) that have longer spacers between the maleimide and the carbohydrate core were synthesized (FIG. 2). Briefly, four amino functionalities were introduced into the tetra-O-allyl derivative (2) by photoaddition with cysteamine in MeOH (Dubber et al., 1998). Instead of using a large excess of cysteamine hydrochloride as previously reported (Dubber et al., 1998), we used only 3 molar equivalent per OH of cysteamine hydrochloride and monitored the reaction by measuring $^1$H-NMR. When the reaction is proceeding, the signals at δ5.10-6.05 (for the allyl groups) decrease and the new signals at δ2.68-2.90 (for $SCH_2$) increase. After disappearance of the allyl signals, the resulting product (8) was readily isolated in 80% yield by SEPHADEX G-15 gel filtration chromatography. We found that using less cysteamine hydrochloride did not affect the efficiency of the reaction but greatly facilitated the purification of the product by gel filtration. Treatment of 8 with methoxycarbonylmaleimide gave the tetravalent maleimide cluster (9) in 71% yield after chromatographic purification. On the other hand, coupling amine (8) with the N-hydroxylsuccinimide ester of 6-maleimidohexanoic acid afforded the tetravalent maleimide cluster (10) in 43% yield (FIG. 2).

EXAMPLE 3

Figure 3:
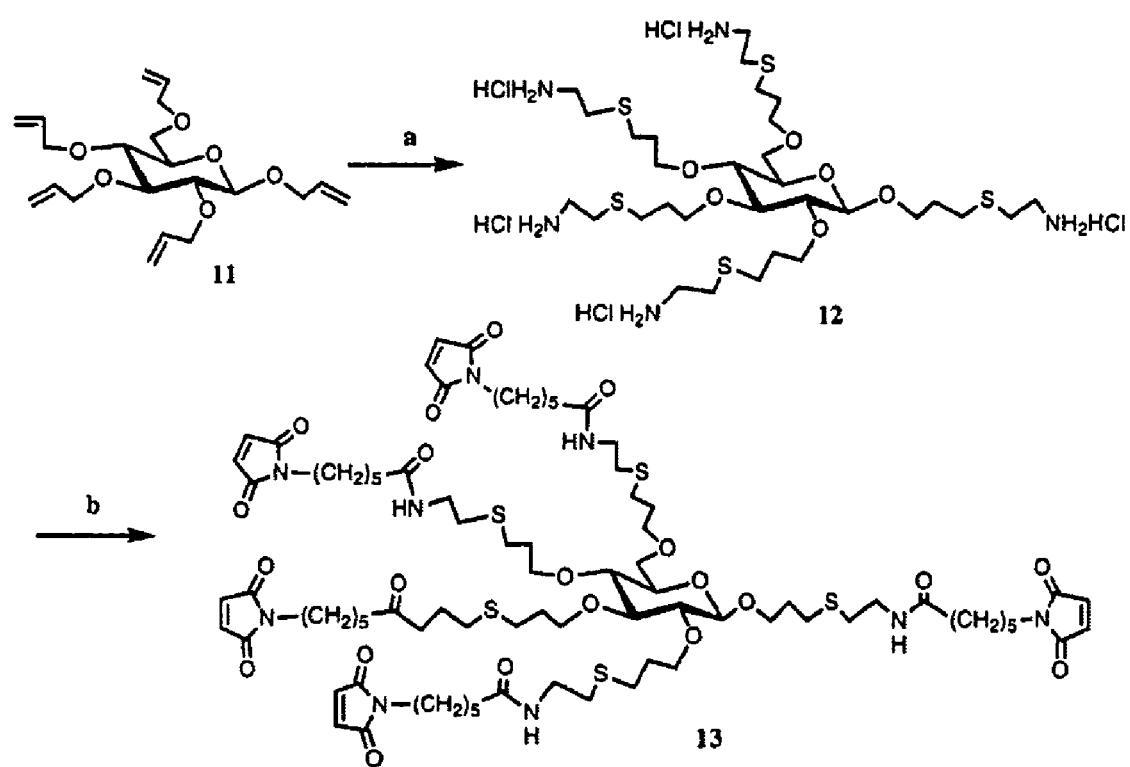
FIG. 3. Synthesis of a β-glucopyranoside-based, pentavalent maleimide cluster with spacers between the carbohydrate core and the maleimide. (a) cysteamine hydrochloride, MeOH, hv, room temp., 80%; (b) 6-maleimidohexanoic acid N-hydroxylsuccinimide ester, 1 M aqueous $NaHCO_3$, THF, 0° C.-room temp., 39%.

The established synthetic schemes are equally useful for the synthesis of maleimide clusters on different carbohydrate cores, which will allow the presentations of peptide chains in distinct orientations as well as in different valencies. As an example, a β-glucopyranoside-based, pentavalent maleimide cluster was readily synthesized (FIG. 3). Briefly, the penta-O-allyl β-glucoside (11), which was prepared according to the reported procedure (Leydet et al., 1997), was converted into the amino-compound (12) in 80% yield by photoaddition with cysteamine. Compound (12) was then reacted with the N-hydroxylsuccinimide ester of 6-maleimidohexanoic acid, giving the penta-valent maleimide cluster (13) in 39% yield (FIG. 3).

EXAMPLE 4

Figure 4:
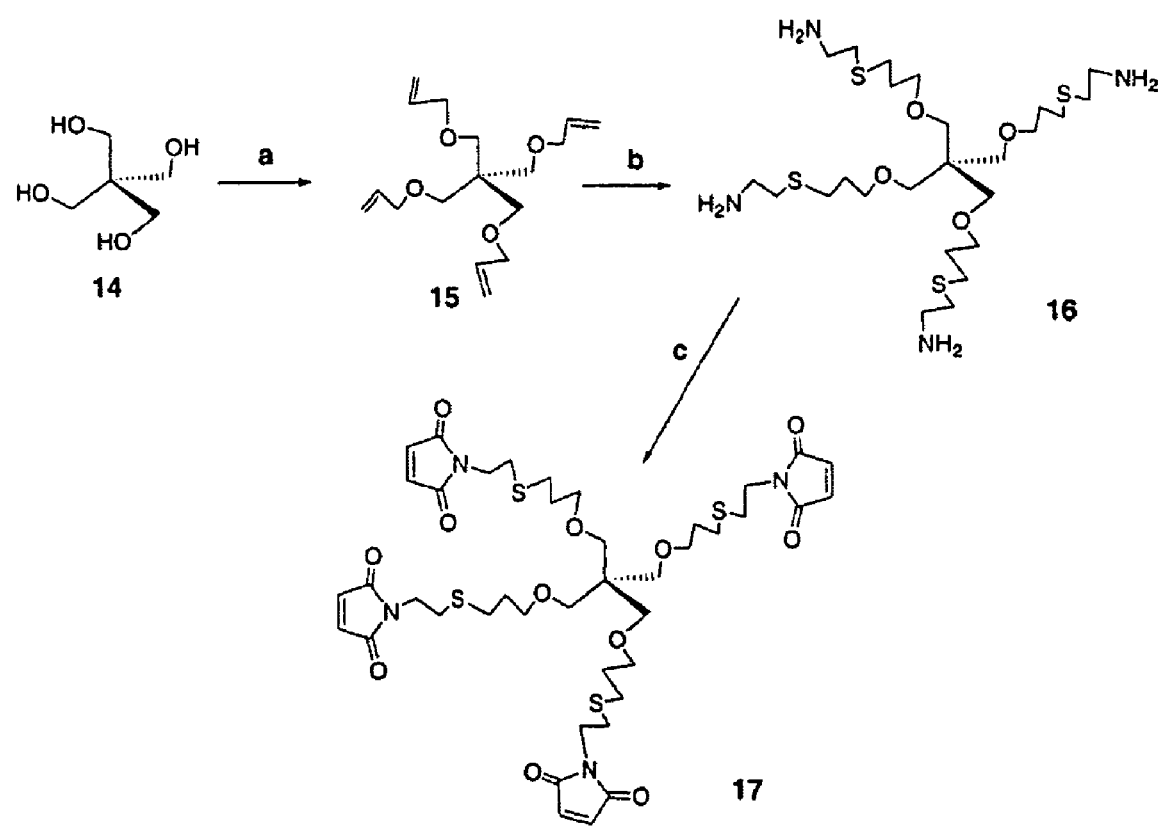
FIG. 4. Synthesis of a tetravalent maleimide cluster based upon pentaerythritol. (a) NaH/DMF, allyl bromide, 0° C.-room temp., 91%; (b) cysteamine, AIBN, MeOH, UV (254 nm), room temp., 84%; (c) Methoxycarbonylmaleimide, 1M aqueous $NaHCO_3$, MeCN, room temp., 50%.

The scaffold is not limited to sugar molecules. Other organic molecules can also be used as the core to prepare maleimide clusters through appropriate chemical modifications. As shown in FIG. 4, pentaerythritol (14) was efficiently converted into a tetravalent maleimide cluster (17) by three chemical steps in high yields. In contrast to carbohydrate-centered maleimide clusters that present the maleimide functionalities in an asymmetric three-dimensional fashion, compound 17 presents the four maleimide functionalities in a non-discriminating spatial arrangement. Both types of presentations will be useful for different purposes.

EXAMPLE 5

Figure 5:
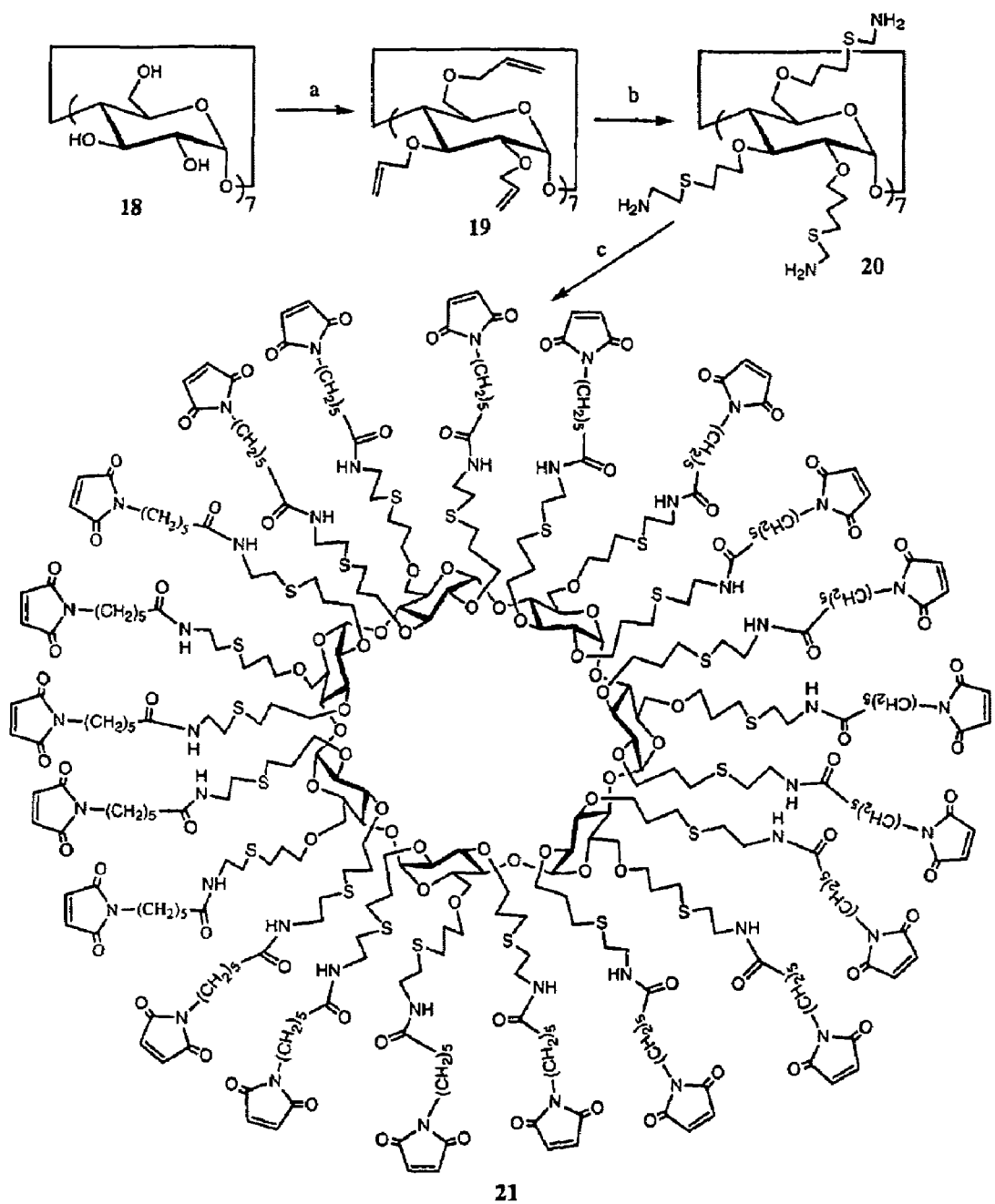
FIG. 5. Synthesis of a β-cyclodextrin-centered, dendritic cluster comprising 21 maleimide functionalities. (a) NaH/DMF, allyl bromide, 0° C.-room temp., 91%; (b) cysteamnine, AIBN, MeOH, UV (254 nm), room temp., 68%; (c) N-hydroxylsuccinimide ester of 6-maleimidohexanoic acid, 1M aqueous $NaHCO_3$, THF, 0° C.-room temp., 51%.

A special class of oligosaccharides, the cyclodextrins, was exploited as the scaffold for the construction of multivalent maleimide clusters. FIG. 5 showed the synthesis of β-cyclodextrin-centered, dendritic cluster that has 21 maleimide functionalities arranged along the ridge of the two faces of the cyclodextrin molecules. Briefly, multiple amino functionalities were introduced into β-cyclodextrin by our established procedures (allylation and subsequent photoaddition) to give the polyamine 20 (Ni et al., 2002). This polyamine was then reacted with the N-hydroxylsuccinimide ester of 6-maleimido-hexanoic acid to provide the cyclodextrin-centered maleimide cluster (21)(FIG. 5). This is the biggest maleimide cluster so far described that has a well-defined chemical structure.

EXAMPLE 6

Figure 6:
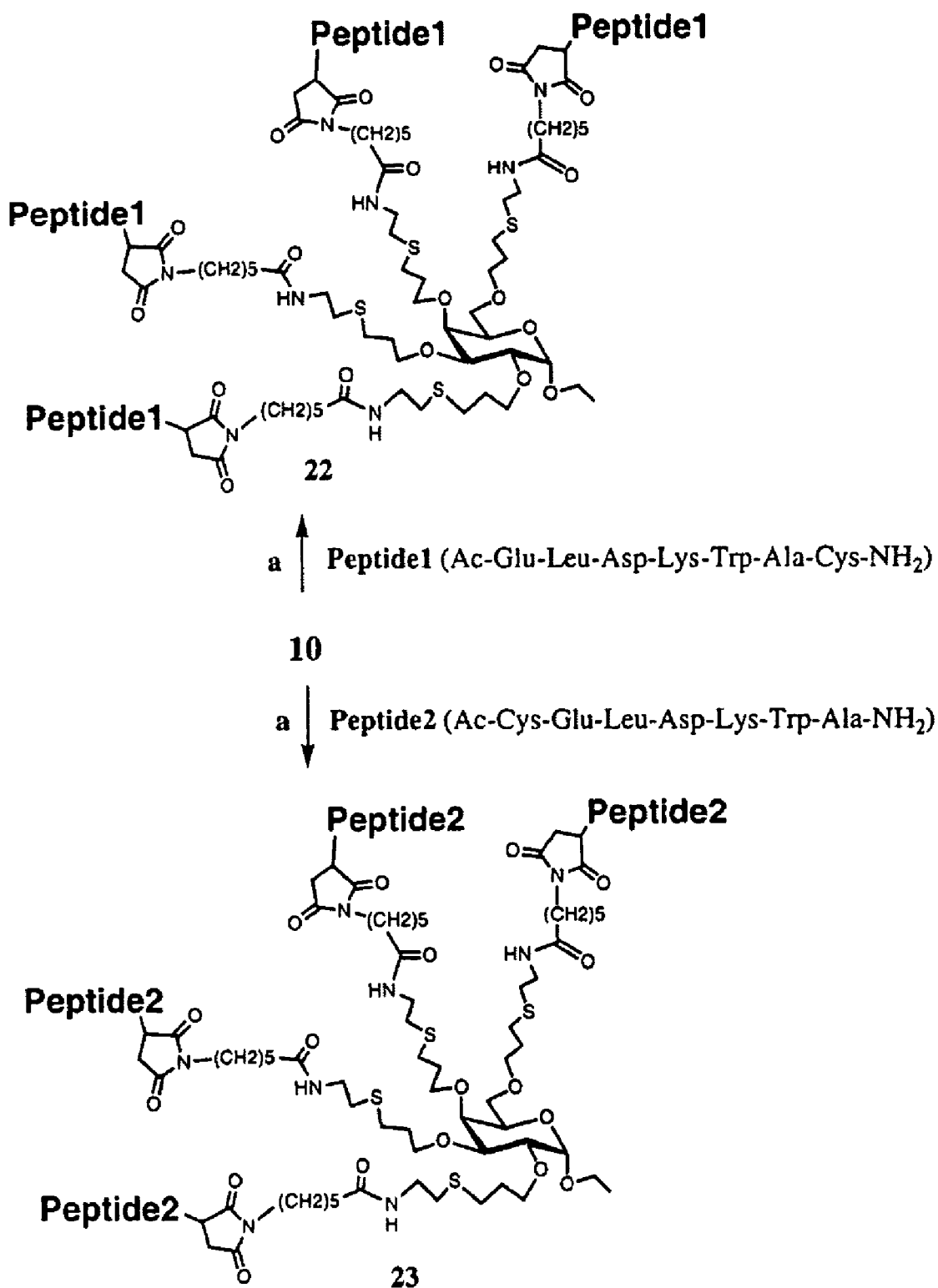
FIG. 6. Ligation of a tetravalent maleimide cluster with peptides of the sequence Ac-ELDKWAC (SEQ ID NO: 1) or Ac-CELDKWA (SEQ ID NO: 2). (a) phosphate buffer (50 mM, pH 6.5-7.5), room temp., Yields: 91% for 22; 88% for 23.

To examine the usefulness of the synthetic maleimide clusters for multivalent peptide assembling, we first set to prepare two multiple antigenic peptides, using 2F5's epitope ELDKWA (SEQ ID NO: 4) as the model peptides. 2F5 is one of the few broadly neutralizing antibodies isolated that can neutralize various primary HIV-1 strains. The neutralizing epitope of 2F5 was mapped to be ELDKWA (SEQ ID NO: 4)(Muster et al., 1993) For the coupling, a cysteine residue was introduced into the epitope sequence either at the C-terminus (peptide 1) or the N-terminus (peptide 2) during the solid phase peptide synthesis. As expected, the ligation between peptide 1 and the malemiide scaffold 10 is extremely fast and efficient at neutral pH at ambient temperature (FIG. 6). A simple HPLC purification gave the tetravalent peptide 22 in 91% yield. We also found that the ligation reaction is equally efficient between pH 6.5-7.5 in an aqueous buffer, which is particularly useful for different peptides that may behave differently under distinct pH. Similarly, the coupling of 10 with the peptide2 that has the cysteine residue at the N-terminus gave the tetravalent 23 in high yield (FIG. 6).

EXAMPLE 7

Figure 7:
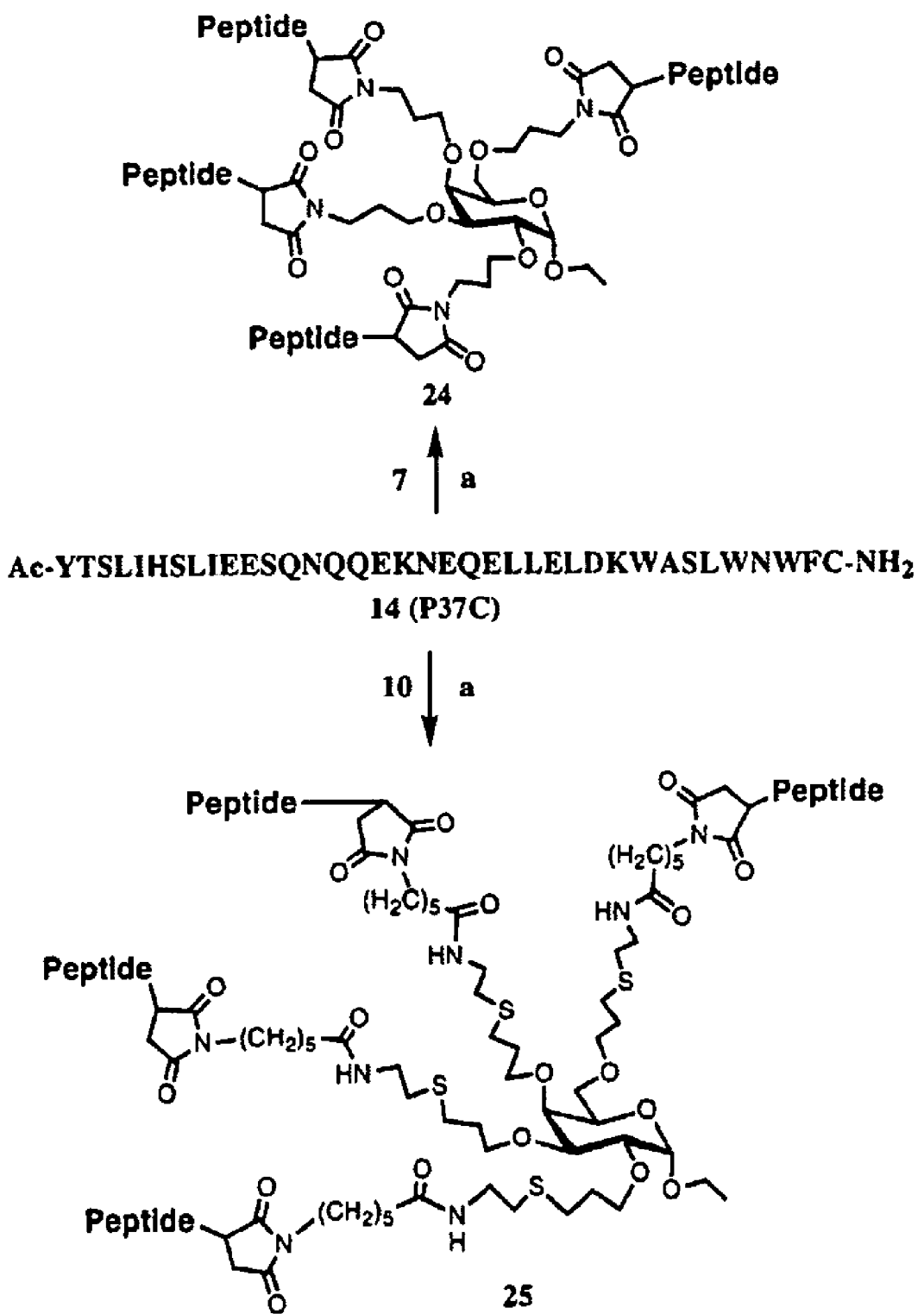
FIG. 7. Ligation of peptides of the sequence Ac-YTSLIH-SLIEESQNQQEKNEQELLELDKWASLWNWFC (SEQ ID NO: 3) with the carbohydrate-centered tetravalent maleimide clusters. (a) 1:1 MeCN-phosphate buffer (pH 7.0), room temp., Yields: 82% for 25; 84% for 26.

The maleimide clusters are equally applicable for larger and more complex peptides. Accordingly, the tetravalent gp41 peptides 25 and 26, each of which contains 4 strands of the 36-mer HIV-1 gp41 peptide DP178 (T20) were synthesized (FIG. 7). The peptide exhibits potent and broadly inhibitory activities against different strains of HIV through blocking viral membrane fusion (Wild et al., 1993; Wild et al., 1994), and is currently in clinical trials for the treatment of AIDS (Kilby et al., 1998). In order to ligate the peptide to the maleimide cluster, a cysteine residue was introduced at the C-terminus of the peptide during solid phase peptide synthesis. The cysteine-containing peptide (24) was thus synthesized using the Fmoc chemistry and purified by reverse phase HPLC. While peptide (24) is insoluble in aqueous buffers below pH 6.5, it is readily soluble under neutral to slightly alkaline conditions (pH 7.0-7.5). Interestingly, the initial attempt to ligate the peptide (24) with the maleimide cluster (7) in a phosphate buffer (50 mM, pH 7.2) failed to give the desired tetravalent peptide. The reaction resulted in a polymer-like solid that, after lyophilization, can hardly dissolve again in aqueous buffers or aqueous organic solvents, or in pure organic solvents such as DMF and acetonitrile. Reverse phase HPLC analysis of the reaction mixture reveals a very broad peak following the peak of peptide (24). Mass spectrometric analysis of the solid failed to give any useful information. We assume that the solid material may result from aggregation of the peptide, which has a concentration of 1 mM in the reaction buffer. The clustered maleimide may serve as a cross-link reagent for the non-covalently aggregating peptides, promoting further and eventually irreversible aggregations of the peptides. It was previously revealed that, in aqueous buffer (pH 7.0), T20 is monomeric at the concentration below 10 μM, but exhibits complicated monomer/tetramer equilibrium and other aggregation patterns when the concentration is above 20 μM. (11) We also observed that, under native gel filtration conditions (PBS, pH 7.2) and at 0.5 mM, both T20 and the synthetic peptide (24) appear as a series of broad peaks that have molecular weights corresponding to the oligomeric and polymeric forms of the parent peptides (data not shown), indicating that indeed the peptides form aggregates at relatively high concentrations.

We eventually found that the ligation of peptide (24) and the maleimide cluster (7) can proceed very smoothly in a 1:1 acetonitrile-phosphate buffer (pH 7.0) to give the desired tetravalent peptide (25)(FIG. 7). In the presence of high concentration of acetonitrile, the peptide could exist in monomeric form. The ligation is rapid and highly efficient. HPLC monitoring indicates that the reaction is actually finished within 30 min. The tetravalent peptide (25) was purified in 82% yield by reverse phase HPLC, and the purity and identity of the product was confirmed by analytic HPLC and ES-MS, respectively.

Similarly, ligation of the peptide (24) to a different template, the tetravalent maleimide cluster (10), under the same reaction conditions as described for the synthesis of 25 gave the tetravalent gp41 peptide (26) in 84% yield after preparative HPLC (FIG. 7).

EXAMPLE 8

Synthesis of Cholic Acid-Based Maleimide Clusters

Figure 8:
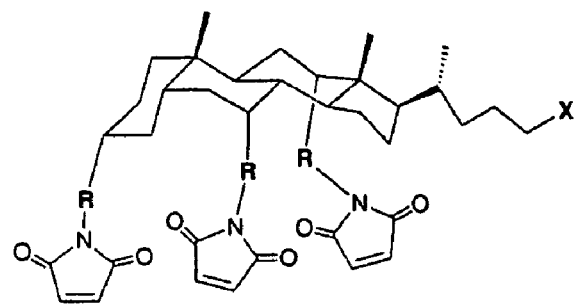
FIG. 8. General structures of cholic acid-based maleimide clusters.

Cholic acid is a rigid, amphiphilic steroid. The hydrophilic face contains 3 hydroxyl groups at defined spatial orientations at 3α, 7α, and 12α positions. Therefore, cholic acid and other bile acids have been used as scaffolds for combinatorial chemistry (Madder et al, 2002; Zhou, et al, 2000) and for the development of antimicrobial agents (Guan, et al, 2000). We have exploited the potential of chloic acid for multivalent peptide construction through the synthesis of cholic acide-based maleimide clusters, the general structures of which were shown in FIG. 8.

Figure 9:
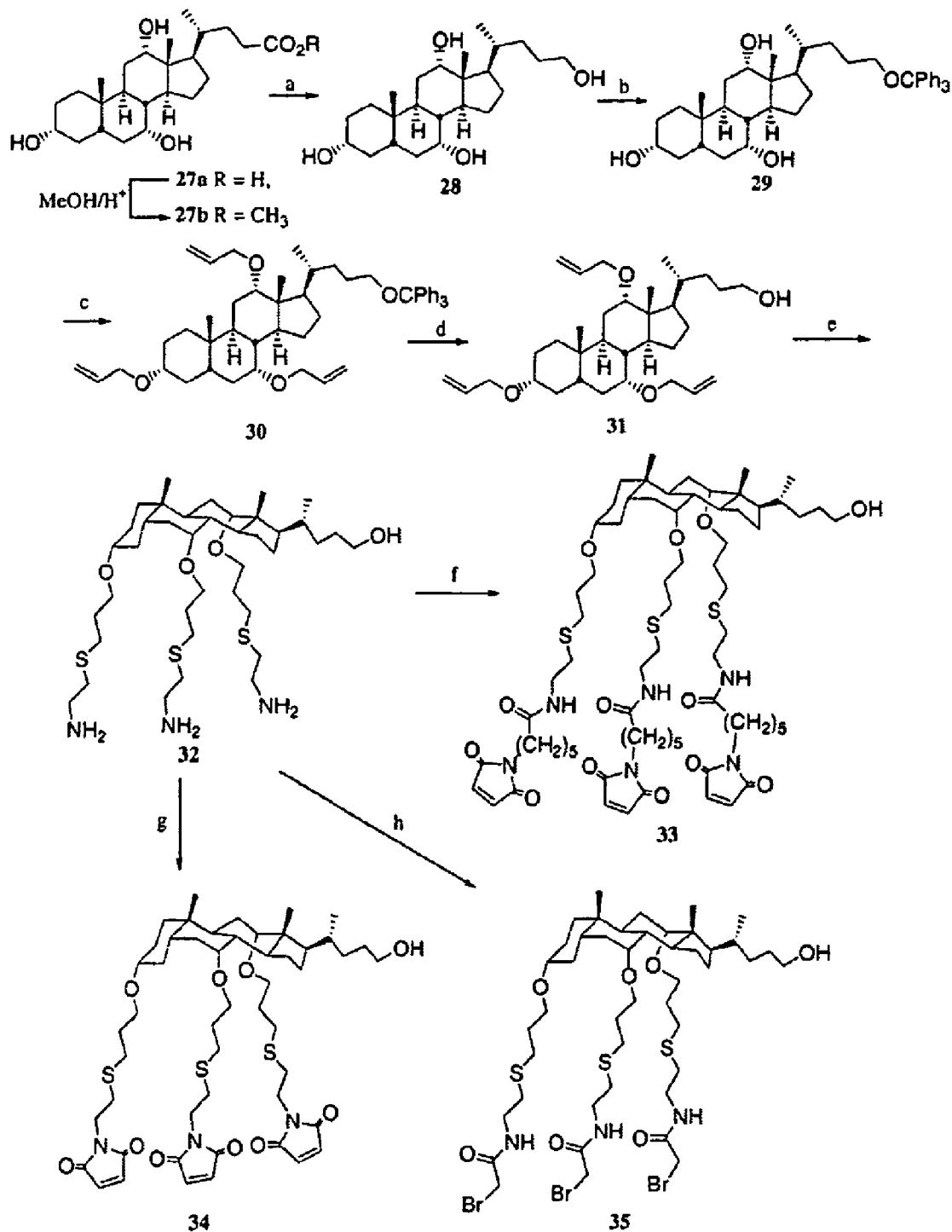
FIG. 9. Synthesis of typical cholic acid-based maleimide clusters. (a) LiAlH4, THF, 0° C. to rt, 98%; (b) Trityl chloride, Et3N, DBU, DMF, rt, 93%; (c) Allyl iodide, NaH, THF, rt to 70° C., 96%; (d) p-Toluenesulfonic acid, DCM, MeOH, 100%; (e) 2-aminoethanethiol hydrochloride, ABIN, MeOH, UV (254 nm), rt, 96%; (f) 6-maleimidohexanoic acid N-hydroxylsuccinimide ester, DCM, rt 76%; (g) N-methoxycarbonylmaleimide, Et3N, DMF, rt 78%, (h) Bromoacetic anhydride, DCM, rt, 89%; or Bromoacetic anhydride, MeCN/$NaHCO_3$ (pH 8.5, 50:50), rt, 96%.

Through selective chemical transformations of functional groups on chloric acid, several novel maleimide clusters were synthesized, in which the maleimide functionality was installed in a defined spatial orientation. This is particularly important because the orientation of the maleimide groups will determine the spatial orientation of the peptide chains attached. The synthesis was summarized in FIG. 9. Briefly, three amine functionalities were selectively introduced at the positions of the 3 hydroxyl groups in cholic acid 27 to give compound 32. Then three maleimide functionalities were attached to afford the maleimide clusters 33 and 34, with long and short spacers, respectively. Similarly, a bromoacetyl group was introduced at each amino group in compound 32 to give the bromoacetyl derivative 35 (FIG. 9), which was prepared for the comparison of the efficiency in ligation.

EXAMPLE 9

Figure 10:
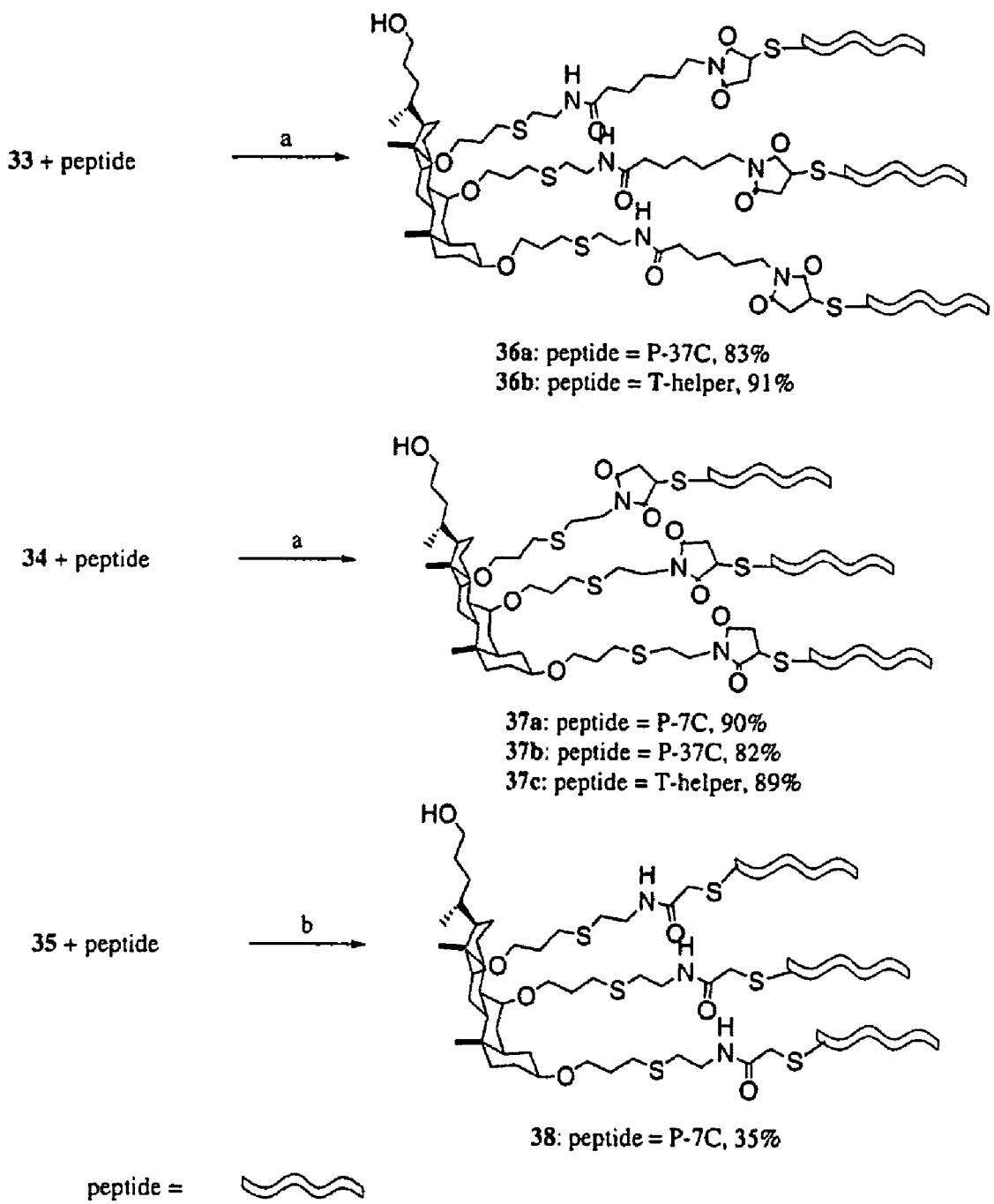
FIG. 10. Ligation of peptides to the cholic acid-based maleimide clusters and the bromoacetyl derivatives. (a) phosphate buffer (pH 6.6)/MeCN (50:50), rt; (b) borate buffer (pH 8.5)/MeCN (50:50), rt.

Ligation of Peptides with the Cholic Acid-Based Maleimide Clusters and the Comparison with the Corresponding Bromoacetyl Derivative Similar to the peptide ligation with the carbohydrate-based clusters, the peptide ligation of the cholic acid-based clusters was found to be highly efficient. As shown in FIG. 10, three different peptides were chosen and tested for the ligation. These include the HIV inhibitor DP178 (P37C), a T-helper epitope from tetanus toxoid (830-844), and a minimum epitope sequence ELDKWA (SEQ ID NO: 4) for HIV-neutralizing antibody 2F5. In the case of the T-helper sequence, a tetra-peptide spacer GSSS was introduced at the N-terminus to increase the aqueous solubility of the otherwise hydrophobic T-helper epitope. Regardless the length and complexity of the peptides, the peptide ligation to the cholic acid-based maleimide clusters gave the desired multivalent peptide clusters (36a, 36b, 37a, 37b, and 37c) in very high yields (FIG. 10).

However, when the bromoacetyl template 35 was used, no ligation product could be obtained for the long peptide P37C. In the case of simple, short peptide ELDKWAC (SEQ ID NO: 1), the yield of the desired ligation product 38 was isolated in only 35% yield under optimal ligation conditions, together with mono- and di-substituted by-products. The results clearly show that the maleimide clusters are superior to other functionalized templates for multivalent peptide assembly.

EXAMPLE 10

Conformational Studies of the Synthetic Multivalent Peptides Using CD Spectroscopy.

Figure 11:
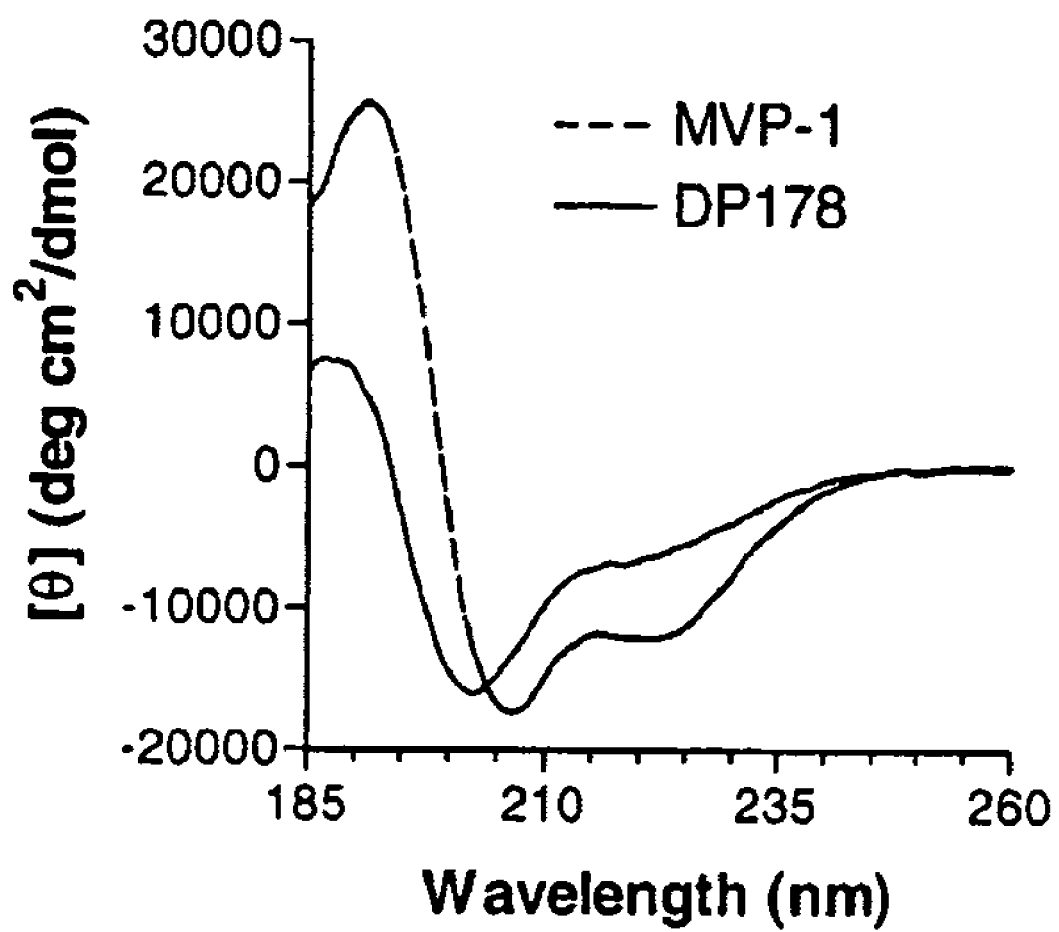
FIG. 11. CD spectra of the MVP-1 and DP178. The spectra were recorded with 10 uM of DP178 and 2.5 uM of MVP-1 in a phosphate buffer (50 mM, pH 7.4) at 23° C.

One application of the scaffolds is to induce special conformations of peptides. The circular dichroism (CD) spectra of the synthetic multivalent gp41 peptide (MVP-1) and peptide DP178 were recorded and compared (FIG. 11). It was shown that the multivalent assembling has a significant impact on the peptide conformation, leading to a great increase of the α-helical content for the peptide. Based on $[\theta]_{222}$ and the proposed formula (Lyu et al, 1991), the content of α-helix was 18% for peptide DP178, which is consistent with the value reported in literature (Lawless et al, 1996), whereas the α-helix content for MVP-1 is 40%. The results suggest that the novel scaffold approach not only allows novel spatial presentation of the gp41 peptides, but also impacts the conformations of the peptides.

Similarly, we measured the circular dichroism (CD) spectra of the cholic acid-based multivalent peptides (36a and 37b). The or-helix contents of 36a and 37b were found to be 41 and 36%, respectively. In other words, the template-assembled peptides form a three-α-helix structure. Again, the results indicate that the spatially defined maleimide clusters are useful templates for constructing suitable ax-helix bundles, which should be valuable for de novo artificial protein design.

EXAMPLE 11

Immunization Studies

Figure 12:
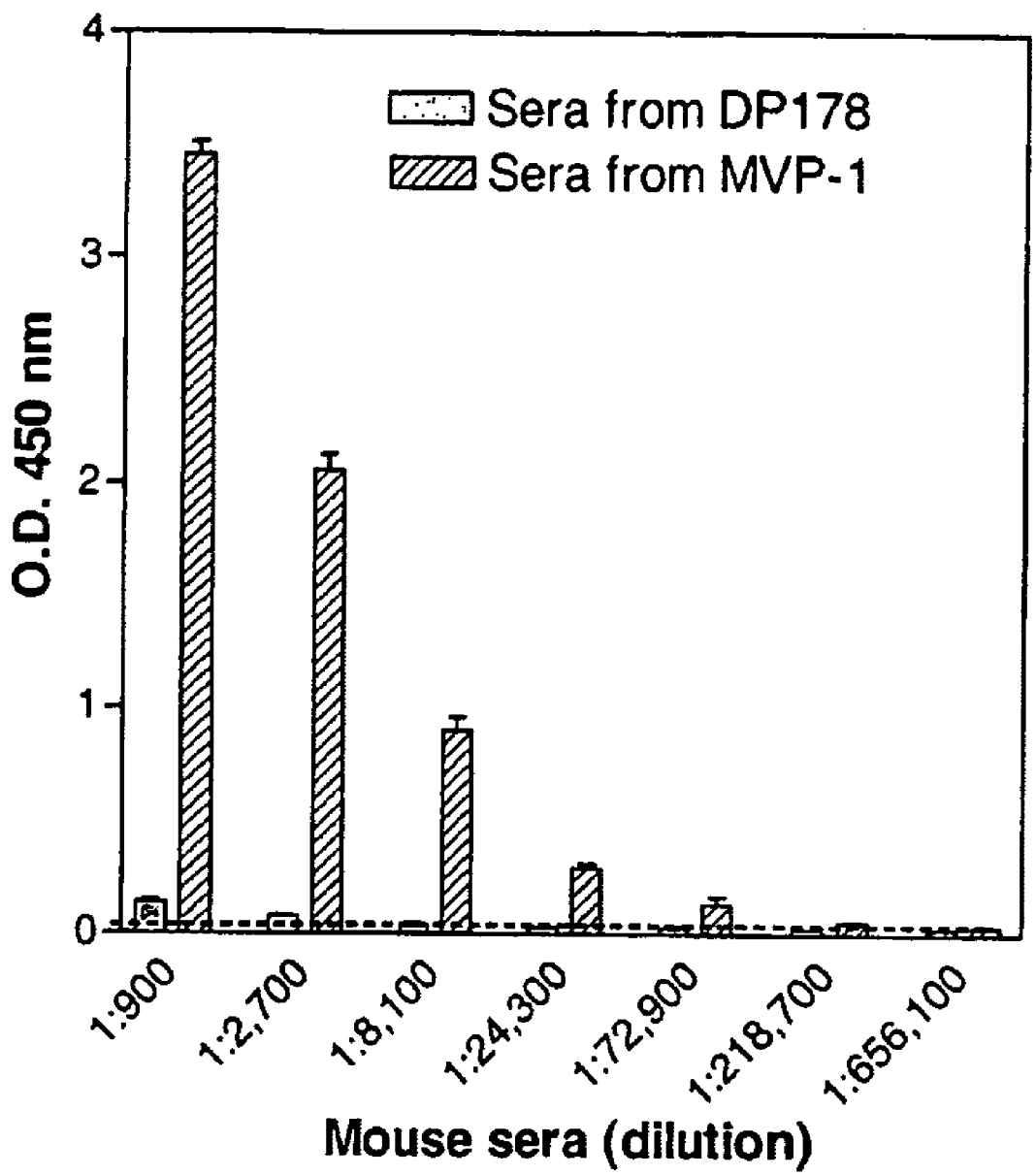
FIG. 12. Antibody titers of the sera from MVP-1-immunized mice against immobilized DP178 at 1 month. BALB/c mice (5 per group) were injected intraperitoneally (i.P.) at days 0, 7, 14, and 21 with 10 ug of immunogens without any adjuvant. The sera were collected 10 days after the last boost and used for the ELISAs.
Figure 13:
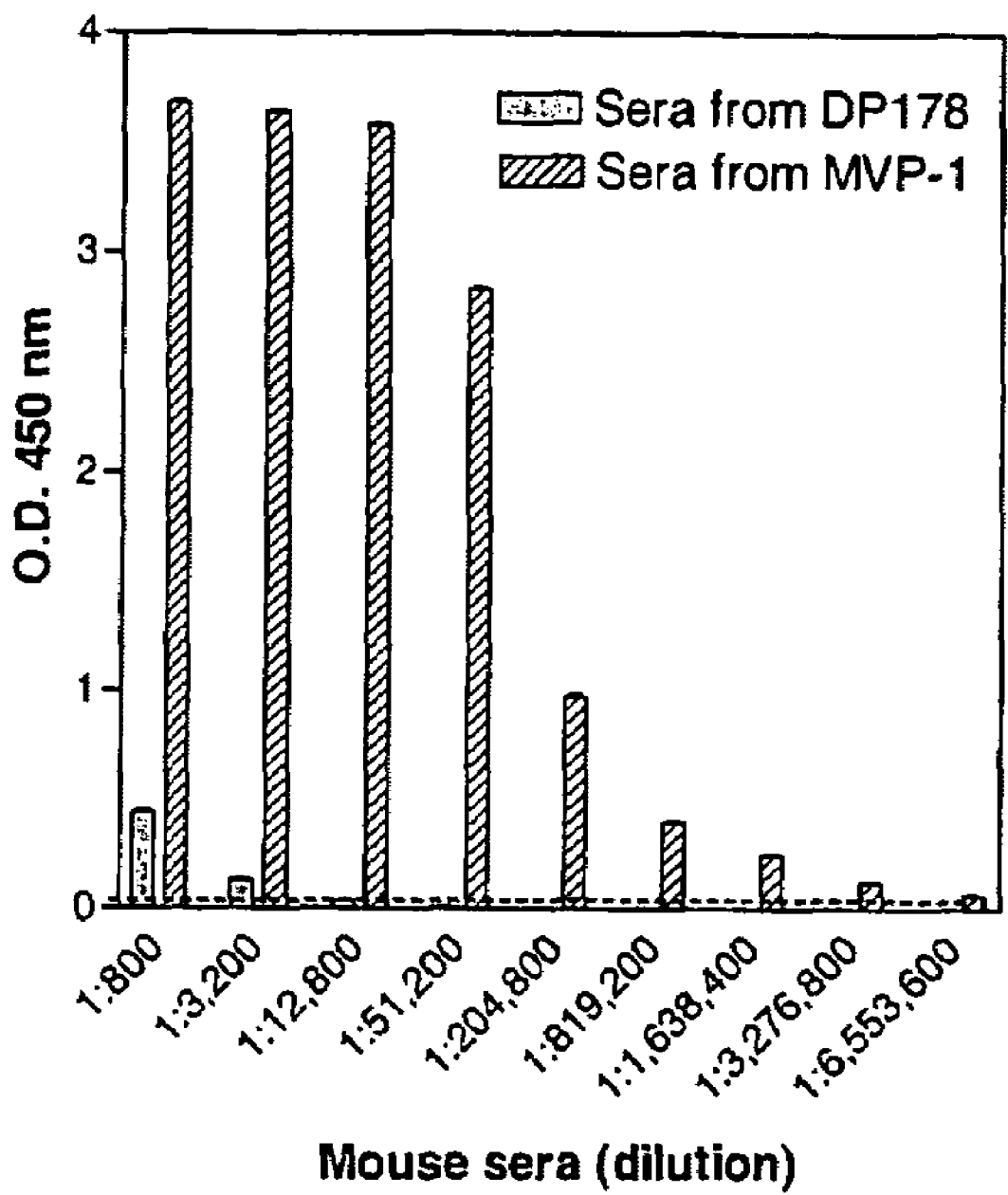
FIG. 13. Antibody titers of the sera from MVP-1-immunized mice against immobilized DP178 at 8 month. BALB/c mice (5 per group) were boosted at month-8 and sera were collected 10 days after the last boost and used for the ELISAs.

We have synthesized novel template-assembled multivalent peptides to mimic the transition state structures of gp41, using peptide DP178 (i.e., T20) as the model peptide. These multivalent peptides are otherwise difficult to obtain by other ligation methods. A preliminary immunization with MVP-1, which contains 4 strands of peptide DP178, was conducted in mice. Same quantity (10 μg each) of the synthetic MVP-1 and the single peptide DP178 itself were used to immunize/boost mice in order to evaluate and compare their immunogenicity. The antibody responses were evaluated with ELISAs and the results were shown in FIG. 4. The data clearly indicate that the multivalent gp41 peptide MVP-1 is highly immunogenic. It was shown that the multivalent gp41 peptide MVP-1 was able to elicit unusually high titers (over 1 to one million) of antibody responses in the absence of any adjuvant (FIGS. 12 & 13). Since novel conformational epitopes may be induced by the rigid template-based assembling (as revealed by the CD spectroscopic studies), the novel multivalent peptides may elicit antibodies targeting native conformations found in HIV-1 and other pathogenic proteins, offering a great potential for novel vaccine development. Moreover, when a T-helper epitope is incorporated in the construct, no additional adjuvants are required for raising high titers of specific antibodies. An adjuvant-free, fully synthetic vaccine is a huge benefit in vaccine development and is of particular significance in terms of clinic trials in the future.

Experimental Procedures

Fmoc-protected amino acids were purchased from Novabiochem. HATU, DIPEA and Fmoc-PAL-PEG-PS were purchased from Applied Biosystems. HPLC grade acetonitrile was purchased from Fisher Scientific. DMF was purchased from B & J Biosynthesis. All other chemicals were purchased from Aldrich/Sigma and used as received. $^1$H NMR spectra were recorded on QE 300 with Me$_4$Si (δ 0) as the internal standard. The ES-MS spectra were measured on a Waters ZMD mass spectrometer. Analytical TLC was performed on glass plates coated with silica gel 60 F$_{254}$ (E. Merck). Carbohydrates were detected by charring with 10% ethanolic sulfuric acid. Amines were detected by ninhydrin spraying. Flash chromatography was performed on silica gel 60 (200-400 mesh, EM Science). Gel filtration was carried out on SEPHADEX G-15 (Pharmacia) using de-ionized water as the eluent. Photo-addition reactions were carried out in a quartz flask under N$_2$. Analytical HPLC was carried out with a Waters 626 HPLC instrument on a Waters NOVA-PAK C18 column (3.9×150 mm) at 40° C. The column was eluted with a linear gradient of acetonitrile (10-90%) containing 0.1% TFA in 25 min at a flow rate of 1 ml/min. Peptides were detected by UV absorbance at 214 and/or 280 nm. Preparative HPLC was performed with a Waters 600 HPLC instrument on a Waters C18 column (SYMMETRY300, 19×300 mm) and/or on a DELTA-PAK C18 column [DELTA-PAK RCM 2×(2.5×10 cm)]. The column was eluted with a linear gradient of acetonitrile (10-60%) containing 0.1% TFA at a flow rate of 10 ml/min. The peptides were detected at 214 and/or 280 nm. Purified peptides were lyophilized and kept under nitrogen in a freezer (−20° C.).

The UV absorbance was run on Beckman DU 640 spectrophotometer. CD's spectrums were measured on Jasco-810 (CD-ORD) spectropolarimeter using quartz cuvette of 1 mm path length. The measurement temperature was 25° C.

Ethyl 2,3,4,6-tetra-O-allyl-α-D-galactopyranoside (2). A solution of ethyl α-D-galactopyranoside 1 (416.4 mg, 2.0 mmol) in anhydrous DMF (5 mL) was added dropwise to a stirred suspension of sodium hydride (60% dispersion in mineral oil, 960.0 mg, 24.0 mmol) in anhydrous DMF (15 mL). After 30 min, the reaction mixture was cooled to 0° C., and allyl bromide (2.90 g, 24.0 mmol) was added dropwise. The resulting mixture was stirred for 1 h at 0° C., and 3 h at room temperature. After the mixture was cooled in an ice-bath, excess sodium hydride was quenched by slow addition of methanol (5 mL). The volatiles were evaporated to dryness, and then the residue was mixed with ethyl acetate (150 mL) and washed with brine (3×30 mL). The organic phase was dried over $Na_2SO_4$, filtered, and concentrated. The oily residue was purified by flash chromatography (hexane/EtOAc 85:15) to afford compound 2 (690.0 mg, 94%) as a colorless oil; $R_f$ 0.65 (hexane/EtOAc 7:3); $^1$H-NMR (300 MHz, $CDCl_3$/TMS): δ6.05-5.84 (m, 4H, $OCH_2CH=CH_2$), 5.36-5.10 (m, 8H, $OCH_2CH=CH_2$), 4.94 (d, 1H, J=3.7 Hz, H-1), 4.39 (dd, 1H, J=12.6, 5.6 Hz, $OCHHCH=CH_2$), 4.30-3.98 (m, 7H, $OCH_2CH=CH_2$), 3.93 (dd, 1H, J=7.1, 6.4 Hz, H-5), 3.84 (s, 1H, br, H-4), 3.83 (dd, 1H, J=9.8, 3.7 Hz, H-2), 3.80-3.60 (m, 2H, H-3, and $OCHHCH_3$), 3.64-3.55 (m, 2H, H-6 and $OCHHCH_3$), 3.52 (dd, 1H, J=9.0, 6.1 Hz, H-6'), 1.24 (t, 3H, J=7.1 Hz, $OCH_2CH_3$); ES-MS: 391.36 $(M+Na)^+$, 323.32 $(M-OEt)^+$, 207.14 $(M+2Na)^{2+}$.

Ethyl 2,3,4,6-tetra-O-(3-hydroxypropyl)-α-D-galactopyranoside (3). To a stirred solution of 2 (230.0 mg, 0.62 mmol) in dry THF (10 mL) was added dropwise a solution of 9-BBN in THF (0.5 M, 10.0 mL, 5.0 mmol) at room temperature. The reaction mixture was heated under reflux for 2 h, and excess of 9-BBN was then destroyed by dropwise addition of water at 0° C. The hydroboration mixture was oxidized by treatment with 3 M aqueous NaOH (11.0 mL) and 30% $H_2O_2$ solution (11.0 mL) at 0° C., followed by stirring overnight at room temperature. The mixture was saturated with $K_2CO_3$, and the phases were separated. The aqueous phase was extracted with THF 2×30 mL) and the combined organic phases were dried over $Na_2SO_4$, filtered, and concentrated. The oily residue was purified by column chromatography (ethyl acetate/Methanol 8:2) to yield tetraol 3 (231.0 mg, 84%) as a colorless oil; $R_f$ 0.49 (EtOAc/MeOH 7:3); $^1$H-NMR ($D_2O$): δ5.10 (d, 1H, J=3.4 Hz, H-1), 4.02 (dd, 1H, J=5.8, 4.8 Hz, $OCHHCH_2CH_2OH$), 3.94 (s, 1H, br, H-4), 3.86-3.50 (m, 22H, H-2, H-3, H-5, H-6, H-6', $OCH_2CH_2CH_2OH$, $OCH_2CH_2CH_2OH$ and $OCH_2CH_3$), 1.86-1.75 (m, 8H, $OCH_2CH_2CH_2OH$), 1.19 (t, 3H, J=7.1 Hz, $OCH_2CH_3$); ES-MS: 463.45 $(M+Na)^+$, 441.47 $(M+H)^+$, 395.43 $(M-OEt)^+$, 243.26 $(M+2Na)^{2+}$.

Ethyl 2,3,4,6-tetra-O-(3-azidopropyl)-α-D-galactopyranoside (5). To a stirred solution of $Ph_3P$ (1.00 g, 3.81 mmol) in dry DMF (3 mL) was added iodine (0.97 g, 3.81 mmol). After 10 min, a solution of tetraol 3 (210.0 mg, 0.48 mmol) in DMF (2 mL) was added dropwise. The resulting mixture was stirred for 2 h at room temperature and another 2 h at 80° C. Heating was then discontinued and the mixture was concentrated under reduced pressure to remove DMF. The residue was purified by flash chromatography (hexane/EtOAc 8:2) to give tetraiodide 4 (293.0 mg, 70%). The iodide 4 thus obtained was used immediately for the next step. Iodide 4: $R_f$ 0.65 (hexane/EtOAc 7:3); $^1$H-NMR ($CDCl_3$/TMS): 84.97 (d, 1H, J=3.4 Hz, H-1), 3.96-3.83 (m, 2H, H-4, and $OCHHCH_2I$), 3.80~3.47 (m, 14H, H-2, H-3, H-5, H-6, H-6', $OCH_2CH_2CH_2I$, and $OCH_2CH_3$), 3.36-3.24 (m, 8H, $OCH_2CH_2CH_2I$), 2.20-1.98 (m, 8H, $OCH_2CH_2CH_2I$), 1.23 (t, 3H, J=7.1 Hz, $OCH_2CH_3$).

A mixture of iodide 4 (260.0 mg, 0.30 mmol) and $NaN_3$ (1.24 g, 19.07 mmol) in dry DMF (10 mL) was stirred overnight at room temperature. The mixture was evaporated at reduced pressure to dryness, and the residue was partitioned in $CH_2Cl_2$ (100 mL) and water. The organic layer was washed with brine (3×20 mL), dried ($Na_2SO_4$), filtered, and concentrated. The oily residue was purified by flash chromatography (hexane/EtOAc 8:2) to provide tetraazide 5 (124.0 mg, 78%); $R_f$ 0.41 (hexane/EtOAc 7:3); $^1$H-NMR ($CDCl_3$/TMS): 84.95 (d, 1H, J=3.4 Hz, H-1), 3.96-3.85 (m, 2H, H-4, and $OCHHCH_2CH_2N_3$), 3.80~3.47 (m, 14H, H-2, H-3, H-5, H-6, H-6', $OCH_2CH_2CH_2N_3$, and $OCH_2CH_3$), 3.47-3.35 (m, 8H, $OCH_2CH_2CH_2N_3$), 1.95-1.76 (m, 8H, $OCH_2CH_2CH_2N_3$), 1.25 (t, 3H, J=7.1 Hz, $OCH_2CH_3$) ); ES-MS: 563.39 $(M+Na)^+$, 467.42 $(M-OEt-N_2)^+$.

Ethyl 2,3,4,6-tetra-O-(3-aminopropyl)-α-D-galactopyranoside (6). Azide 5 (61.0 mg, 0.11 mmol) was hydrogenated with Pd/C (10%, 10 mg) in methanol (5 mL) overnight at room temperature. The mixture was filtered through a bed of CELITE, and the filtrate was then concentrated to give tetraamine 6 (51.5 mg, 100%); $^1$H-NMR ($D_2O$): δ5.10 (d, 1H, J=3.4 Hz, H-1), 4.06-3.98 (m, 1H, $OCHHCH_2CH_2NH_2$), 3.96-3.92 (m, 1H, H-4), 3.90~3.48 (m, 14H, H-2, H-3, H-5, H-6, H-6', $OCH_2CH_2CH_2NH_2$, and $OCH_2CH_3$), 2.89-2.70 (m, 8H, $OCH_2CH_2CH_2NH_2$), 1.90-1.65 (m, 8H, $OCH_2CH_2CH_2NH_2$), 1.18 (t, 3H, J=7.1 Hz, $OCH_2CH_3$); ES-MS: 437.48 $(M+H)^+$, 219.16 $(M+2H)^{2+}$.

Ethyl 2,3,4,6-tetra-O-(3-maleimidopropyl)-α-D-galactopyranoside (7). A solution of amine 6 (17.8 mg, 0.04 mmol) in 1 M aqueous solution of $NaHCO_3$ (1 mL) was treated with methoxycarbonylmaleimide (37.94 mg, 0.24 mmol) at 0° C. After 5 min, the mixture was diluted with water (1 mL) and acetonitrile (2 mL), and then stirred at room temperature for 4 h. After adding $CH_2Cl_2$ (50 mL), the organic layer was separated and washed with brine (3×10 mL). The organic layer was then dried ($Na_2SO_4$), filtered, and concentrated. The oily residue was purified by flash chromatography ($CH_2Cl_2$/MeOH 95:5) to give maleimide 7 (23.2 mg, 76%); $R_f$ 0.42 ($CH_2Cl_2$/MeOH 95:5); $^1$H-NMR ($CDCl_3$/TMS): δ6.70 (s, 2H, CH=CH), 6.69 (s, 4H, CH=CH), 6.68 (s, 2H, CH=CH), 4.98 (d, 1H, J=3.4 Hz, H-1), 3.95-3.82 (m, 2H, H-4, and $OCHHCH_2CH_2N$), 3.80~3.35 (m, 22H, H-2, H-3, H-5, H-6, H-6', $OCH_2CH_2CH_2N$, $OCH_2CH_2CH_2N$, and $OCH_2CH_3$), 1.96-1.78 (m, 8H, $OCH_2CH_2CH_2N$), 1.25 (t, 3H, J=7.1 Hz, $OCH_2CH_3$); ES-MS: 779.28 $(M+Na)^+$, 401.29 $(M+2Na)^{2+}$.

Ethyl 2,3,4,6-tetra-O-(6-amino-3-thia-hexyl)-α-D-galactopyranoside tetrahydrochloride (8). To a solution of the tetra-O-allyl derivative 2 (404.6 mg, 1.10 mmol) and AIBN (30.0 mg) in methanol (15 mL) in a Quartz flask was added cysteamine hydrochloride (1.50 g, 13.20 mmol). After being degassed by bubbling $N_2$ into solution for 30 min, the resulting mixture was stirred and irradiated (UV, 254 nm) under $N_2$. The reaction was monitored by measuring the $^1$H-NMR of a small portion of the reaction mixture, which was dried and deuterium-exchanged with $D_2O$ before recording the NMR. During the progress of the reaction, the signals at δ5.10-6.05 (for the allyl groups) decreased and the new signals at δ2.68-2.90 (for $SCH_2$) increased. After 24 h, NMR indicated the disappearance of the allyl signals. MeOH was then evaporated and the residue was purified by gel filtration on a SEPHADEX G-15 column using water as the eluent. Fractions containing the product were pooled and lyophilized to give amine 8 (723.4 mg, 80%) as a colorless glass-like solid; $^1$H-NMR ($D_2O$): δ5.08 (d, 1H, J=3.4 Hz, H-1), 4.0-3.98 (m, 1H, $OCHHCH_2CH_2S$), 3.96-3.92 (m, 1H, H-4), 3.90~3.48 (m, 14H, H-2, H-3, H-5, H-6, H-6', $OCH_2CH_2CH_2S$, and $OCH_2CH_3$), 3.26~3.14 (m, 8H, $SCH_2CH_2NH_2HCl$), 2.90-2.82 (m, 8H, $SCH_2CH_2NH_2HCl$), 2.72-2.68 (m, 8H, OCH$_2$CH$_2$CH$_2$S), 1.96-1.78 (m, 8H, OCH$_2$CH$_2$CH$_2$S) 1.20 (t, 3H, J=7.1 Hz, OCH$_2$CH$_3$); ES-MS: 677.1 (M+H-4HCl)$^+$, 339.1 (M+2H-4HCl)$^{2+}$.

Ethyl 2,3,4,6-tetra-O-(6-maleimido-3-thia-hexyl)-α-D-galactopyranoside (9). A solution of amine 8 (23.9 mg, 29.0 μmol) dissolved in 1 M aqueous solution of NaHCO$_3$ (1 mL) was treated with methoxycarbonylmaleimide (27.03 mg, 17.4 μmol) at 0° C. After 5 min, the mixture was diluted with water (1 mL) and acetonitrile (2 mL), and then stirred at room temperature for 1 h. The mixture was diluted with CH$_2$Cl$_2$ (50 mL) and washed with brine (3×10 mL). The organic phase was dried over Na$_2$SO$_4$, filtered and concentrated. The oily residue was purified by flash chromatography (CH$_2$Cl$_2$/MeOH 96:4) to give maleimide 9 (20.3 mg, 71%); R$_f$ 0.45 (CH$_2$Cl$_2$/MeOH 96:4); $^1$H-NMR (CDCl$_3$/TMS): δ6.72 (s, 8H, CH=CH), 4.94 (d, 1H, J=3.4 Hz, H-1), 3.95-3.82 (m, 2H, H-4, and OCHHCH$_2$CH$_2$N), 3.80~3.45 (m, 22H, H-2, H-3, H-5, H-6, H-6', OCH$_2$CH$_2$CH$_2$S, SCH$_2$CH$_2$N, and OCH$_2$CH$_3$), 2.90-2.60 (m, 16H, OCH$_2$CH$_2$CH$_2$SCH$_2$CH$_2$N), 1.96-1.82 (m, 8H, OCH$_2$CH$_2$CH$_2$S), 1.23 (t, 3H, J=7.1 Hz, OCH$_2$CH$_3$); ES-MS: 1019.49 (M+Na)$^+$, 951(M-OEt)$^+$.

Ethyl 2,3,4,6-tetra-O-[(6-(6-maleimidohexanamido)-3-thia-hexyl)]-α-D-galactopyranoside (10). A solution of amine 8 (138.6 mg, 0.17 mmol) in 1 M aqueous solution of NaHFCO$_3$ (1.5 mL) was added dropwise to a stirred solution of 6-maleimidohexanoic acid N-hydroxysuccinimide ester (272.5 mg, 0.88 mmol) in THF (3 mL), which was cooled with a bath of ice-water. The resulting mixture was stirred for 1 h at 0-5° C. The mixture was then diluted with CHCl$_3$ (70 mL) and washed with brine (3×10 mL). The organic phase was dried over Na$_2$SO$_4$, filtered, and concentrated. The oily residue was purified by flash chromatography (CH$_2$Cl$_2$/MeOH 95:5) to give maleimide 10 (103.6 mg, 43%); R$_f$ 0.62 (CH$_2$Cl$_2$/MeOH 9:1); $^1$H-NMR (CDCl$_3$/TMS): δ 6.68 (s, 8H, CH=CH), 6.26-6.20 (m, 2H, NH), 6.12 (t, 1H, J=6.8 Hz, NH), 6.04 (t, 1H, J=6.8 Hz, NH), 4.92 (d, 1H, J=3.2 Hz, H-1), 3.95-3.86 (m, 2H, H-4, and OCHHCH$_2$CH$_2$N), 3.80~3.40 (m, 30H, H-2, H-3, H-5, H-6, H-6', OCH$_2$CH$_2$CH$_2$S, SCH$_2$CH$_2$N, NCH$_2$(CH$_2$)$_4$ and OCH$_2$CH$_3$), 2.75-2.60 (m, 16H, OCH$_2$CH$_2$CH$_2$SCH$_2$CH$_2$N), 2.18 (t, 8H, J=7.3 Hz, N(CH$_2$)$_4$CH$_2$), 1.96-1.82 (m, 8H, OCH$_2$CH$_2$CH$_2$S), 1.74-1.54 (m, 16H, NCH$_2$CH$_2$CH$_2$CH$_2$CH$_2$), 1.37-1.24 (m, 8H, N(CH$_2$)$_2$CH$_2$(CH$_2$)$_2$), 1.22 (t, 3H, J=7.1 Hz, OCH$_2$CH$_3$); ES-MS: 1450.01 (M+H)$^+$, 725.56 (M+2H)$^{2+}$.

(6-Amino-3-thia-hexyl) 2,3,4,6-tetra-O-(6-amino-3-thia-hexyl)-β-glucopyranoside pentahydrochloride (12). To a solution of penta-O-allyl derivative 11 (12)(628.5 mg, 1.65 mmol) and AIBN (50.0 mg) in methanol (15 mL) in a quartz flask was added cysteamine hydrochloride (2.80 g, 24.67 mmol). After being degassed by bubbling N$_2$ into the solution for 30 min, the resulting mixture was stirred and irradiated (UV, 254 nm) under N$_2$. The reaction was monitored by $^1$H-NMR, After 24 h when NMR showed the disappearance of the allyl signals, the solvent removed by evaporation and the residue was subjected to gel filtration on a column of SEPHADEX G-15 using water as the eluent. Fractions containing the product were pooled and lyophilized to give amine 12 (1.25 g, 80%) as a colorless glass-like solid; $^1$H-NMR (D$_2$O): δ4.43 (d, 1H, J=7.8 Hz, H-1), 4.04-3.40 (m, 13H, H-5, H-6, H-6', OCH$_2$CH$_2$CH$_2$S), 3.40 (dd, 1H, J=8.5, 9.1 Hz, H-4), 3.36 (dd, 1H, J=9.1, 9.3 Hz, H-3), 3.26-3.16 (m, 10H, SCH$_2$CH$_2$NH$_2$HCl), 3.11 (dd, 1H, J=7.8, 9.3 Hz, H-2), 2.90-2.82 (m, 10H, SCH$_2$CH$_2$NH$_2$HCl), 2.72-2.64 (m, 10H, OCH$_2$CH$_2$CH$_2$S), 1.96-1.84 (m, 10H, OCH$_2$CH$_2$CH$_2$S); ES-MS: 766.1 (M+H-5HCl)$^+$, 383.7 (M+2H-5HCl)$^{2+}$.

[6-(6-maleimidohexanamido)-3-thia-hexyl]2,3,4,6-tetra-O-[6-(6-maleimidohexanamido)-3-thia-hexyl)-β-D-glucopyranoside (13). A solution of amine 12 (109.8 mg, 0.12 mmol) in 1 M aqueous solution of NaHCO$_3$ (1.2 mL) was added dropwise to a stirred solution of 6-maleimidohexanoic acid N-hydroxylsuccinimide ester (214.2 mg, 0.70 mmol) in THF (3 mL) that was cooled with a bath of ice-water. The resulting mixture was stirred for 1 h at 0-5° C., and then diluted with CHCl$_3$ (70 mL). The organic layer was separated and washed with brine (3×10 mL), dried (Na$_2$SO$_4$), filtered, and concentrated. The oily residue was subjected to column chromatography (CH$_2$Cl$_2$/MeOH 95:5) to give pentamaleimide 13 (76.7 mg, 39%); R$_f$ 0.35 (CH$_2$Cl$_2$/MeOH 95:5); $^1$H-NMR (CDCl$_3$/TMS): δ6.69 (s, 10H, CH=CH), 6.28-6.15 (m, 5H, NH), 4.18 (d, 1H, J=7.8 Hz, H-1), 3.95-3.50 (m, 13H, H-5, H-6, H-6', OCH$_2$CH$_2$CH$_2$S), 3.50 (t, 10H, J=7.2 Hz, NCH$_2$(CH$_2$)$_4$), 3.50-3.38 (m, 10H, SCH$_2$CH$_2$N), 3.24-3.16 (m, 2H, H-3, H-4), 3.04-2.96 (m, 1H, H-2), 2.70-2.58 (m, 20H, OCH$_2$CH$_2$CH$_2$SCH$_2$CH$_2$N), 2.18 (t, 10H, J=7.3 Hz, N(CH$_2$)$_4$CH$_2$), 1.92-1.78 (m, 10H, OCH$_2$CH$_2$CH$_2$S), 1.74-1.54 (m, 20H, NCH$_2$CH$_2$CH$_2$CH$_2$CH$_2$), 1.38-1.24 (m, 10H, N(CH$_2$)$_2$CH$_2$(CH$_2$)$_2$); ES-MS: 1733.16 (M+H)$^+$, 866.84 (M+2H)$^{2+}$.

Tetra-O-allyl pentaerythritol (15). A solution of pentaerythritol 14 (0.68 g, 5.0 mmol) in anhydrous DMF (10 mL) was added dropwise to a stirred suspension of sodium hydride (60% dispersion in mineral oil, 2.01 g, 50.0 mmol) in anhydrous DMF (15 mL). After 30 min, the reaction mixture was cooled to 0° C., and then allyl bromide (4.84 g, 40.0 mmol) was added dropwise with a syringe. The resulting mixture was stirred for 1 h at 0° C., and overnight at room temperature. After the mixture was cooled with an ice bath, the excess sodium hydride was quenched by the slow addition of methanol (5 mL). The volatile was evaporated to dryness, and then the residue was mixed with ethyl acetate (150 mL) and washed with brine (3×30 mL). The organic phase was dried over Na$_2$SO$_4$, filtered, and concentrated. The oily residue was purified through flash chromatography (hexane/EtOAc 97:3) to afford compound 15 (1.34 g, 91%) as a colorless oil; $^1$H-NMR (300 MHz, CDCl$_3$/TMS): δ5.95-5.81 (m, 4H, OCH$_2$CH=CH$_2$), 5.30-5.11 (m, 8H, OCH$_2$CH=CH$_2$), 3.96 (m=s, 4H, OCH$_2$CH=CH$_2$), 3.94 (m=s, 4H, OCH$_2$CH=CH$_2$), 3.46 (s, 8H, CH$_2$OCH$_2$CH=CH$_2$); ESI-MS: 319.32 (M+Na)$^+$, 297.31 (M+H)$^+$.

Tetra-O-6-amino-3-thiahexyl pentaerythritol tetrahydrochloride (16). To a solution of compound 15 (151.4 mg, 0.51 mmol) and AIBN (20.0 mg) in methanol (10 mL) in a Quartz flask was added cysteamine hydrochloride (348.2 mg, 3.06 mmol). After being degassed by bubbling N$_2$ into solution for 30 min, the resulting mixture was stirred and irradiated (UV, 254 nm) under N$_2$ for 24. The volatile was evaporated under reduced pressure, and the residue was then purified by gel filtration on SEPHADEX G-15 using water as eluent. Fractions containing the product were pooled and lyophilized to give compound 16 (319.4 mg, 84%); $^1$H-NMR (D$_2$O): δ3.56 (t, 8H, J=6.1 Hz, CCH$_2$OCH$_2$CH$_2$CH$_2$SCH$_2$CH$_2$NH$_2$HCl), 3.40 (s, 8H, CCH$_2$OCH$_2$CH$_2$CH$_2$SCH$_2$CH$_2$NH$_2$HCl), 3.20 (t, 8H, J=6.6 Hz, CCH$_2$OCH$_2$CH$_2$CH$_2$SCH$_2$CH$_2$NH$_2$HCl), 2.83 (t, 8H, J=6.7 Hz, CCH$_2$OCH$_2$CH$_2$CH$_2$SCH$_2$CH$_2$NH$_2$HCl), 2.63 (t, 8H, J=7.2 Hz, CCH$_2$OCH$_2$CH$_2$CH$_2$SCH$_2$CH$_2$NH$_2$HCl), 1.85 (p, 8H, J=6.7 Hz, CCH$_2$OCH$_2$CH$_2$CH$_2$SCH$_2$CH$_2$NH$_2$HCl); ESI-MS: 627.26 (M+Na-4 HCl)$^+$, 605.30 (M+H-4 HCl)$^+$, 303.18 (M+2H-4HCl)$^{2+}$.

Tetra-O-6-(6-maleimidohexanamido)-3-thiahexyl pentaerythritol (17). A solution of compound 16 (55.4 mg, 73.8 μmol) in 1 M aqueous solution of NaHCO$_3$ (2 mL) was added dropwise to a stirred solution of N-succimidyl 6-maleimidohexanoic acid ester (135.6 mg, 0.44 mmol) in THF (3 mL) cooled with a bath of ice-water. The resulting mixture was stirred for 1 h at 0° C., and then diluted with ethyl acetate (60 mL) and washed with brine (3×10 mL). The organic phase was dried over $Na_2SO_4$, filtered and concentrated. The oily residue was purified through flash chromatography to give compound 17 (47.0 mg, 47%); $^1$H-NMR ($CDCl_3$/TMS): δ 6.89 (s, 8H, CH=CH), 6.12 (t, 4H, J=5.4 Hz, NH), 3.51 (t, 8H, J=7.2 Hz, $CCH_2OCH_2CH_2CH_2S$), 3.48-3.40 (m, 16H, $SCH_2CH_2NH$, $NCH_2(CH_2)_4$), 3.34 (s, 8H, $CCH_2OCH_2CH_2CH_2S$), 2.65 (t, 8H, J=6.4 Hz, $SCH_2CH_2NH$), 2.58 (t, 8H, J=7.4 Hz, $CCH_2OCH_2CH_2CH_2S$), 2.18 (t, 8H, J=7.4 Hz, $NHCOCH_2CH_2CH_2CH_2N$), 1.81 (p, 8H J=6.8 Hz, $OCH_2CH_2CH_2S$), 1.72-1.54 (m, 16H, $NCH_2CH_2CH_2CH_2CH_2$), 1.38-1.24 (m, 8H, $N(CH_2)_2CH_2(CH_2)_2$); ESI-MS: 1399.98 $(M+Na)^+$, 1377.97 $(M+H)^+$, 689.75 $(M+2H)^{2+}$.

Typical procedures for the allylation of cyclodextrins: Each of the cyclodextrins (2 mmol) was dissolved in DMF (15 mL) by heating and stirring. The clear solution was then added dropwise to a cooled (0° C.) suspension of sodium hydride (60% dispersion in mineral oil, 4 equiv. Per OH group in cyclodextrin) that was washed with dry hexane (2×10 ml) before being suspended in DMF (50 mL). After the suspension was stirred at 0-5° C. for 1 h, a solution of allyl bromide (3 equiv. Per OH function) in DMF (10 mL) was added dropwise. The resulting mixture was first stirred at 0-5° C. for 1 h, then at 25° C. for 2-4 h. At this point, TLC showed the formation of a single product. The reaction was quenched by addition of MeOH (5 mL). DMF and excess allyl bromide were removed by evaporation under a reduced pressure. The residue was partitioned between ethyl acetate (200 mL) and water (30 mL). The organic layer was washed with brine (2×50 ml), dried over $Na_2SO_4$, and evaporated. Flash column chromatography of the residue on silica gel using hexane-ethyl acetate (3:1, v/v) as the eluant gave the respective O-per-allylated cyclodextrins.

Per-O-allyl-β-cyclodextrin (19): yield 91%; $R_f$=0.41 (25:1 toluene-EtOH), and 0.31 (3:1 hexane-EtOAc); $[α]_{23D}$=+53° (c 0.5, $CHCl_3$), lit.$_{20}$ $[α]_{25D}$=+92° (c 0.5, $CHCl_3$); $^1$H-NMR ($CDCl_3$/TMS): δ6.16~6.05 (m, 7H, $OCH_2CH=CH_2$), 6.05~5.92 (m, 14H, $OCH_2CH=CH_2$), 5.44~5.29 (m, 21H, $OCH_2CH=CHH$), 5.25 (d, 7H, J=3.4 Hz, H-1), 5.24~5.14 (m, 21H, $OCH_2CH=CHH$), 4.57 (dd, 7H, J=12.1, 5.3 Hz, $OCHHCH=CH_2$), 4.35 (dd, 7H, J=12.1, 5.6 Hz, $OCHHCH=CH_2$), 4.30~4.17 (m, 14H, $OCHHCH=CH_2$), 4.17~4.04 (m, 14H, $OCHHCH=CH_2$), 3.99 (dd, 7H, J=10.5, 2.4 Hz, H-6), 3.92~3.64 (m, 21H, H-3, H-4 and H-5), 3.67 (d, 7 H J=10.5 Hz, H-6'), 3.43 (dd, 7H, J=9.4, 3.4 Hz, H-2); $^{13}$C NMR ($CDCl_3$): 138.84 ($OCH_2CH=CH_2$), 138.00 ($OCH_2CH=CH_2$), 137.52 ($OCH_2CH=CH_2$), 119.36 ($OCH_2CH=CH_2$), 119.30 ($OCH_2CH=CH_2$), 118.19 ($OCH_2CH=CH_2$), 101.33 (C-1), 82.64 (C-3), 81.86 (C-2), 81.68 (C-4), 77.07 ($OCH_2CH=CH_2$), 74.79 ($OCH_2CH=CH_2$), 74.75 ($OCH_2CH=CH_2$), 73.63 (C-5), 71.70 (C-6); ES-MS: 1994.4 $(M-3H_2+Na)^+$, 1977.4 $(M+H)^+$, 1008.4 $(M-3H_2+2Na)^{2+}$, 989.4 $(M+2H)^{2+}$.

Per-O-3-((hydrochloride amino)ethylthio)propyl)-β-cyclodextrin (20). To a solution of 19 (213.0 mg, 0.11 mmmol) and AIBN (20.0 mg) in MeOH (10 mL) in a quartz flask was added cysteamine hydrochloride (771.4 mg, 6.79 mmol). After degassed by bubbling $N_2$ into the solution for 30 min, the resulting mixture was stirred and irradiated (UV 254 nm) under $N_2$ atmosphere. The progress of the reaction was monitored with $^1$H NMR. After 5 days, $^1$H NMR showed the disappearance of allyl proton signals. The volatiles were evaporated under reduced pressure, and the residue was purified by gel filtration on SEPHADEX G-15 using water as the eluent. Fractions containing the product was pooled and lyophilized to give the polyamine hydrochloride 20 (317.0 mg, 68%) as a colorless glass-like solid: $[α]_{23D}$=+22° (c 0.5, $H_2O$); $^1$H NMR ($D_2O$): δ5.35~5.10 (m, 7H, H-1), 4.20~3.50 (m, 70H, $OCH_2CH_2CH_2S$—, H-3, H-5, H-6' and H-6), 3.48~3.32 (m, 14H, H-2 and H-4), 3.30~3.14 (m, 42H, —$CH_2NH_2HCl$), 3.00~2.84 (m, 42H, —$SCH_2CH_2NH_2HCl$), 2.84~2.60 (m, 42H, —$CH_2SCH_2CH_2NH_2HCl$), 2.10~1.85 (m, 42H, —$CH_2CH_2CH_2S$); $^{13}$C NMR ($D_2O$): 101.00~99.00 (C-1), 84.00~80.00 (C-2, C-3, and C-4), 77~73.00(C-5, and C-6), 73.00~70.00 (~$OCH_2CH_2CH_2S$), 41.22 ($SCH_2CH_2NH_2HCl$), 31.92 (—$OCH_2CH_2CH_2S$), 31.23 ($SCH_2CH_2NH_2HCl$), 30.15 ($OCH_2CH_2CH_2S$).

Per-O-6-(6-maleimidohexanamido)-3-thiahexyl)-β-cyclodextrin (21). To the stirred solution of compound 20 (44.6 mg, 10.0 μmol) and N-succinimidyl 6-maleimidohexanoic acid ester (129.5 mg, 0.42 mmol) in methanol (2 mL) was added 1 M aqueous solution of $NaHCO_3$ (1.0 mL) at 0-5° C. The resulting mixture was stirred for 1 h at 0-5° C., and then diluted with Chloroform (60 mL) and washed with water (3×10 mL). The organic phase was dried over $Na_2SO_4$, filtered and concentrated. The oily residue was purified through flash chromatography to give compound 21 (38.6 mg, 51%); $^1$H-NMR (DMSO-$d_6$): δ7.96-7.86 (m, 21H, $SCH_2CH_2NH$), 6.97 (s, 42H, CH=CH), 5.11-5.00 (m, 7H, H-1), 4.00-3.05 (m, 168H, H-2, H-3, H-4, H-5, H-6, H-6', $OCH_2CH_2CH_2SCH_2CH_2NH$, NH(O)$CCH_2CH_2CH_2CH_2CH_2N$), 2.65-2.38 (m, 84H, $OCH_2CH_2CH_2SCH_2CH_2NH$), 2.08-1.97 (m, 42H, NH(O)$CCH_2CH_2CH_2CH_2CH_2N$), 1.88-1.65 (m, 42H, $OCH_2CH_2CH_2S$), 1.60-1.35 (m, 84H, $NCH_2CH_2CH_2CH_2CH_2$), 1.30-1.10 (m, 42H, $N(CH_2)_2CH_2(CH_2)_2$).

Peptide synthesis. All peptides used were synthesized on a Pioneer Peptide Synthesizer (Applied Biosystems, Foster City, Calif.) using Fmoc-chemistry on Fmoc-PAL-PEG-PS resin. 4-Fold excess of $N_α$-Fmoc-protected amino acids were used for each coupling and HATU/DIPEA were used as the coupling reagents. The N-terminus of the peptide was capped with an acetyl group. Cleavage of the peptide from the resin with simultaneous deprotection was performed with TFA: thioanisole:EDT:anisole ((90:5:3:2)(cocktail R), and the crude peptide was precipitated with cold ether. Purification of the peptide was carried out by preparative HPLC as described in the general methods. Using the methods, the following peptides were synthesized and purified.

DP178 containing a cysteine at the C-terminus (P37C), Ac-YTSLIHSLIEESQNQQEKNEQELLELDK-WASLWNWFC-NH2 (SEQ ID NO: 3) retention time (tR), 15.8 min; ESI-MS, 1532.84 (M+3H) 3+, 1149.80 (M+4H) 4+, 920.12 (M+5H)s+.

The minimum epitope of 2F5 (P7C), Ac-ELDKWAC-NH2 (SEQ ID NO: 1) retention time (tR), 13.5 min; ESI-MS, 905.53 (M+H) 1+, 453.42 (M+2H) 2+.

The T-helper epitope derived from tetanus toxoid (830-844), CGSSSQYIKANSKFIGITEL-NH2 (SEQ ID NO: 5) retention time, 13.88 min; ESI-MS: 1431.68 (M+2H) 2+, 1073.90 (M+3H) 3+, 716.42 (M+4H) 4+.

Tetravalent peptide (22). To a solution of Ac-Glu-Leu-Asp-Lys-Trp-Ala-Cys-NH2 (SEQ ID NO: 1)(peptidel)(15 mg, 16.6 mol) in phosphate buffer (50 mM, pH 7.0, 2.0 mL) and acetonitrile (2.0 mL) was added dropwise a solution of maleimide 10 (3.8 mg, 2.6 llmol) in DMF (100 μL). After shaken at room temperature for 1 h, the reaction mixture was lyophilized. The residue was purified by RP-HPLC as described in general methods, giving the tetravalent peptide 22 (12 mg, 91%) as a white powder. ES-MS of 22: 1691.6 (M+3H) 3+, 1269.2 (M+4H) 4+, 1015.8 (M+5) 5+.

Tetravalent peptide (23). To a solution of Ac-Cys-Glu-Leu-Asp-Lys-Trp-Ala-NH2 (SEQ ID NO: 2)(peptide2)(10 mg, 11 mmol) in phosphate buffer (50 mM, pH 7.0, 1.5 mL) and acetonitrile (1.5 mL) was added a solution of maleimide 10 (2.67 mg, 1.83 p, mol) in DMF (210 pal). After 1 h at room temperature, the reaction mixture was lyophilized and the residue was purified by preparative HPLC as described in General Methods to afford the tetravalent peptide 23 (8.2 mg, 88%). ES-MS of 23: 1692.0 (M+3H) 3+, 1270.1 (M+4H) 4+, 1016.1 (M+5) 5+.

Peptide (24). The peptide 24 was synthesized on a PIONEER peptide synthesizer (Applied Biosystems, Foster City, Calif.) using Fmoc-chemistry on Fmoc-PAL-PEG-PS resin. 4-Fold excess of $N^{\alpha}$-Fmoc-protected amino acids were used for each coupling and HATU/DIPEA were used as the coupling reagents. The N-terminus of the peptide was capped with an acetyl group. Cleavage of the peptide from the resin with simultaneous deprotection was performed with TFA: thioanisole:EDT:anisole (90:5:3:2)(cocktail R), and the crude peptide was precipitated with cold ether. Purification of the peptide was carried out by preparative HPLC as described in the general methods. The purified 24 appeared as a single peak on analytic HPLC. Under the analytic conditions (General Methods), the peptide was eluted at 15.84 min. ES-MS of 24: 1532.84 $(M+3H)^{3+}$, 1149.80 $(M+4H)^{4+}$, 920.12 $(M+5H)^{5+}$.

Tetravalent peptide (25). To a solution of peptide 24 (20.0 mg, 4.35 µmol) in phosphate buffer (50 mM, pH 7.0, 3.0 mL) and acetonitrile (3.0 mL) was added dropwise a solution of maleimide 7 (0.52 mg, 0.69 µmol) in DMF (104 µL). After shaken at room temperature for 2 h, the reaction mixture was lyophilized. The residue was purified by RP-HPLC as described in general methods, giving the tetravalent peptide 25 (10.7 mg, 82%) as a white powder. Analytical HPLC showed that the purified 25 showed up at 16.47 min as a single peak. ES-MS of 25: 1914.75 $(M+10H)^{10+}$, 1741.00 $(M+11H)^{11+}$, 1596.01 $(M+12H)^{12+}$, 1473.36 $(M+13H)^{13+}$, 1368.29 $(M+14H)^{14+}$, 1276.76 $(M+15H)^{15+}$.

Tetravalent peptide (26). To a solution of peptide 24 (20.0 mg, 4.35 µmol) in phosphate buffer (50 mM, pH 7.0, 3.0 mL) and acetonitrile (3.0 mL) was added a solution of maleimide 10 (1.05 mg, 0.72 µmol) in DMF (210 µL). After 2 h at room temperature, the reaction mixture was lyophilized and the residue was purified by preparative HPLC as described in General Methods to afford the tetravalent peptide 26 (12 mg, 84%). Analytical HPLC showed a single peak for 26 with a retention time of 16.85 min. ES-MS of 26: 1653.72 $(M+12H)^{12+}$, 1526.60 $(M+13H)^{13+}$, 1417.63 $(M+14H)^{14+}$, 1323.20 $(M+15H)^{15+}$.

3α, 7α, 12α, 24-tetra-Hydroxcholane (28). To a suspension of LiAlH$_4$ (3.85 g, 100 mmol) in 100 mL dry THF was added dropwise a solution of methyl ester 27b (15.03 g, 35 mmol) in 200 mL dry THF in 30 min under nitrogen with vigorously stirring in an ice bath. The react mixture was then stirred at room temperature overnight. Celite (3.00 g) was added to the sluggish mixture. The precipitate was removed via filtration and washed with hot methanol. The filtrate was concentrated under vacuum to 80 mL. Another 150 mL acetone was added to recrystallize. After filtration and washing with acetone, 28 was obtained as a whit solid (13.20 g, 98%). $^1$H NMR (500 MHz, CDCl$_3$/TMS) δ 3.96 (bs, 1H, HO—C(12)), 3.82 (bs, 1H, HO—C(7)), 3.79 (d, 2H, J=2.5 Hz, H$_2$—C(24)), 3.25 (b, 1H, HO—C(24)), 3.21 (m, 1H, H—C(12)), 3.15 (m, 1H, H—C(7)), 3.07 (m, 1H, H—C(3)), 2.15-1.10 (series of multiplet, 25H), 0.92 (d, 3H, J=6.5 Hz, H$_3$C—C(20)), 0.89 (s, 3H, H$_3$C—C(10)), 0.65 (s, 3H, H$_3$C—C(13)); ES-MS: 789.47 $(2×M+H)^+$, 395.58 $(M+H)^+$.

3α, 7α, 12α-tri-hydroxyl-24-trityloxyl-5β-cholane (29). Compound 28 (6.23 g, 15.8 mmol) was mixed with trityl chloride (6.60 g, 23.7 mmol) and dissolved in 100 mL DMF. To this mixture was added Et$_3$N (10 mL) and DBU (0.90 g, 5.9 mmol) with stirring at room temperature. After 24 hours reaction, 400 mL water was added, and the mixture was stirred vigorously for 2 hours. The precipitate was collected via filtration and washed with acetone. The crude product was re crystallized in 50 mL acetone, after filtration and washing cold acetone, a white solid 29 was provided (9.35 g, 93%). $^1$H NMR (300 MHz, CDCl$_3$/TMS) δ 7.43 (d, 6H, J=7.3 Hz, phenyl H-2, H-6), 7.29-7.18 (m, 9H, phenyl H-3, H-4, H-5), 3.96 (bs, 1H, H—C(12)), 3.82 (bs, 1H, H—C(7)), 3.41 (m, 1H, H—C(3)), 3.00 (m, 2H), 2.92 (s, 2H), 2.87 (s, 2H), 2.19 (m, 2H), 2.04 (s, 1H), 1.98-1.00 (series of multiplet, 16H), 0.96 (d, 3H, J=6.1 Hz, H$_3$C—C(20)), 0.86 (s, 3H, H$_3$C—C(10)), 0.64 (s, 3H, H$_3$C—C(13)).

3α, 7α, 12α-tri-pentaoxyl-24-trtyloxyl-5β-cholane (30). Sodium hydride (60% in mineral oil, 2.00 g, 29.2 mmol) was added to a solution of compound 29 (3.12 g, 4.8 mmol) in mL dry THF in portion under N$_2$, and stirred for 2 hours at room temperature. The mixture was heated to 70° C., allyl iodide (4.98 g, 30.0 mmol) was added dropwise in 10 min and then the mixture was stirred for 4 hours. After cooled to room temperature, 30 mL ethyl acetate was added to dilute, followed by adding 20 mL water. The organic layer was washed with H$_2$O (2×20 mL) and brine, and dried over anhydrous Na$_2$SO$_4$. After removing the solvent under vacuum the residue was purified on flash column chromatography with elution of hexane/ethyl acetate (90:10). A pale yellow syrup-like 30 was obtained (3.49 g, 96%). $^1$H NMR (300 MHz, CDCl$_3$/TMS) δ 7.44 (d, 6H, J=7.1 Hz, benzyl H-2, H-6), 7.29-7.20 (m, 9H, benzyl H-3, H-4, H-5), 5.88 (m, 3H, HC=CH$_2$), 5.23 (m, 3H, HHC=CHC), 5.11 (m, 3H, HHC=CHC), 4.13 (m, 4H, OH$_2$CHC=CH$_2$, (C-7, C-12)), 3.99 (bs, 2H, OH$_2$CHC=CH$_2$, C-3), 3.88-3.50 (series of multiplet, 6 H), 3.35 (t, 2H, J=8.3 Hz, H$_2$—C(24)), 3.32 (bs, 1H, H—C(12)), 3.16 (m, 1H, H—C(7)), 3.03 (m, 1H, H—C(3)), 3.07 (m, 1H, H—C(3)), 2.30-1.02 (series of multiplet, 18H), 0.92 (d, 3H, J=6.0 Hz, H$_3$C—C(20)), 0.89 (s, 3H, H$_3$C—C(10)), 0.66 (s, 3H, H$_3$C—C(13)).

3α, 7α, 12α-tri-pentaoxyl-24-hydroxyl-5β-cholane (31). p-Toluenesulfonic acid (45.0 mg, 0.23 mmol) was added to a solution of compound 30 (1.20 g, 1.6 mmol) dissolved in mixture of 40 mL DCM and 10 mL methanol. The mixture was stirred at room temperature overnight, after diluted with DCM (20 mL) the mixture was washed with 0.5 NaHCO$_3$ (15 mL), H$_2$O (2×15 mL) and brine. The organic layer was dried over anhydrous Na$_2$SO$_4$, concentrated under vacuum. The residue was separated by flash column chromatography with elution of hexane/ethyl acetate (70:30) to give 31 as a colorless syrup (0.83 g, 100%). $^1$H NMR (500 MHz, CDCl$_3$/TMS) δ 5.91 (m, 3H, HC=CH$_2$), 5.25 (m, 3H, HHC=CHC), 5.11 (m, 3H, HHC=CHC), 4.07 (d, 2H, J=12.5 Hz, OH$_2$CHC=CH$_2$, (C-12)), 4.00 (d, 2H, J=5.5 Hz, OH$_2$CHC=CH$_2$, (C-7)), 3.77 (dt, 1H, J=7.5, 5.0 Hz, HH—C(24)), 3.71 (ddd, 1H, J=6.0, 4.5, 1.5 Hz, HH—C(24)), 3.61 (b, 2H, OH$_2$CHC=CH$_2$, (C-3)), 3.54 (bs, 1H, H—C(12)), 3.32 (d, 1H, J=2.5 Hz, H—C(7)), 3.13 (m, 1H, H—C(3)), 2.26 (dd, 1H, J=13.0, 12.0 Hz, H—C(11)), 2.18 (ddd, 1H, J=8.0, 8.0, 4.0 Hz, H—C(8)), 2.01 (dd, 1H, J=10.0, 9.5 Hz, H—C(11)), 1.87-0.96 (series of multiplet, 24H), 0.92 (d, 3H, J=6.5 Hz, H$_3$C—C(20)), 0.89 (s, 3H, H$_3$C—C(10)), 0.65 (s, 3H, H$_3$C—C(13)); $^{13}$C NMR (500 MHz, CDCl$_3$/TMS) 136.26, 116.45, 115.69, 95.00, 80.98, 79.34, 75.07, 68.58, 69.47, 68.93, 63.93, 63.90, 46.58, 46.55, 42.81, 42.25, 42.23, 40.03, 35.76, 35.62, 35.60, 35.24, 35.23, 32.02, 29.69, 29.11, 28.22, 27.86, 27.69, 23.44, 23.22, 18.03, 12.79; ESI-MS calcd. For C$_{33}$H$_{55}$O$_4$$^+$ (M+H)$^+$: 515.40; found: 1029.80 (2×M+H)$^+$, 515.57 (M+H)$^+$, 457.52 (M−58+H)$^+$, 399.47 (M−2×58+H)$^+$, 341.47 (M−3×58+H)$^+$.

3α, 7α, 12α-tri-(6-Amino-3-thia-hexy-oxyl)-24-hydroxyl-5β-cholane (32). To a mixture of compound 31 (300 mg, 0.58 mmol) and 2-aminoethanethiol hydrochloride (397 mg, 3.50 mmol) in 20 mL methanol contained by a Quartz flask was added ABIN (9.4 mg, 0.057 mmol). The solution was degassed by bubbling N$_2$, and irradiated by UV (254 nm) with stirring under N$_2$ overnight. 30 mL DCM was added to dilute, and the reaction mixture was washed with 0.5 M NaHCO$_3$ (2×10 mL), H$_2$O (2×5 mL) and brine. The organic layer was dried over anhydrous NaSO$_4$, concentrated under vacuum. The crude residue was separated over flash chromatography with gradient elution of ethyl acetate/methanol (0:100 to 100:0), to give 32 as a glass-like solid (415 mg, 96%). $^1$H NMR (500 MHz, CDCl$_3$/TMS) δ 3.74 (m, 1H, H—C(24)), 3.68 (m, 1H, H—C(24)), 3.61 (m, 2H, OCH$_2$CCH$_2$CH$_2$S), 3.56 (bs, 2H, OCH$_2$CCH$_2$CH$_2$S), 3.53 (t, 2H, J=7.0 Hz, OCH$_2$CCH$_2$CH$_2$S), 3.35 (m, 7H, CH$_2$CH$_2$NH$_2$, HO—C(24)), 3.22 (m, 1H, H—C(12)), 3.16 (m, 7H, NCH$_2$CH$_2$S, H—C(7)), 3.06 (m, 1H, H—C(3)), 2.86 (m, 6H, OCH$_2$CH$_2$CH$_2$S), 2.74 (m, 3H, OCH$_2$CHHCH$_2$S), 2.68 (t, 3H, J=7.0 Hz, OCH$_2$CHHCH$_2$S), 2.20-1.05 (series of multiplet, 32H), 0.98 (d, 3H, J=6.0 Hz, H$_3$C—C(20)), 0.94 (s, 3H, H$_3$C—C(10)), 0.72 (s, 3H, H$_3$C—C(13)); $^{13}$C NMR (500 MHz, CDCl$_3$/TMS) 80.82, 79.95, 76.15, 66.19, 65.82, 62.47, 47.36, 46.46, 46.29, 42.86, 42.10, 40.64, 39.87, 38.91, 38.86, 35.72, 35.45, 35.12, 34.82, 32.11, 30.14, 29.93, 29.83, 28.93, 28.79, 28.61, 28.54, 28.47, 28.33, 28.00, 27.65, 27.59, 23.32, 22.72, 22.16, 17.52, 17.13, 14.47, 11.75; ESI-MS calcd. for C$_{39}$H$_{76}$N$_3$O$_4$S$_3$$^+$ (M+H)$^+$: 746.49; found: 746.58 (M+H)$^+$, 373.98 (M+2H)$^{2+}$.

3α, 7α, 12α-tri-[6-(6-maleimidohexanamido-3-thia-hexyoxyl)]-24-hydroxyl-5β-cholane (33). To a solution of free amine 32 (7.2 mg, 9.6 μmol) in 10 mL DCM was added 6-maleimidohexanoic acid N-hydroxylsuccinimide ester (30 mg, 96 μmol). The mixture was stirred at room temperature for 3 hours, TLC showed no more free amine remained in the reaction mixture. The solvent was removed under vacuum, and the residue was purified through flash chromatography with elution of ethyl acetate/methanol (95:5) to give 33 as a colorless oil was provided (9.6 mg, 76%). $^1$H NMR (500 MHz, CDCl$_3$/TMS) δ 6.72 (s, 6H, HC=CH), 6.61 (t, 1H, J=6.5 Hz, HN), 6.48 (t, 1H, J=6.5 Hz, HN), 6.19 (t, 1H, J=6.5 Hz, HN), 3.59 (td, 2H, J=13.0, 6.5 Hz, H$_2$—C(24)), 3.52 (t, 6H, J=7.0 Hz, OCH$_2$CCH$_2$CH$_2$S), 3.47 (bs, 6H, CH$_2$CH$_2$NCO) 3.43 (m, 6H, NCH$_2$CH$_2$S), 3.25 (b, 1H, HO—C(24)), 3.21 (m, 1H, H—C(12)), 3.15 (m, 1H, H—C(7)), 3.07 (m, 1H, H—C(3)), 2.66-2.59 (m, 12H, OCH$_2$CH$_2$CH$_2$S, SCH$_2$CH$_2$N), 2.18 (m, 6H, NCOCH$_2$CH$_2$), 2.15-1.06 (series of multiplet, 48H), 0.92 (d, 3H, J=6.5 Hz, H$_3$C—C(20)), 0.89 (s, 3H, H$_3$C—C(10)), 0.65 (s, 3H, H$_3$C—C(13)); $^{13}$C NMR (500 MHz, CDCl$_3$/TMS) 174.7, 174.7, 174.7, 164.5, 164.5, 164.5, 164.5, 164.5, 164.5, 136.6, 136.6, 136.6, 136.6, 136.6, 136.6, 85.5, 75.4, 72.4, 67.5, 67.2, 66.9, 63.3, 49.9, 48.2, 45.1, 45.1, 45.1, 43.3, 41.5, 40.8, 40.8, 40.8, 39.4, 37.6, 36.8, 35.3, 34.9, 34.9, 34.5, 34.5, 34.5, 34.3, 34.3, 34.3, 33.3, 33.3, 33.3, 31.6, 31.0, 29.7, 29.1, 29.1, 29.0, 28.3, 28.3, 28.3, 28.1, 27.0, 26.4, 26.4, 26.4, 25.7, 25.7, 25.7, 25.2, 18.5, 12.5; ESI-MS calcd. for C$_{69}$H$_{109}$N$_6$O$_{13}$S$_3$$^+$ (M+H)$^+$: 1326.71; found: 1348.09 (M+Na)$^+$, 1326.17 (M+H)$^+$, 663.82 (M+2H)$^{2+}$.

3α, 7α, 12α-tri-(6-Maleimido-3-thia-hexy-oxyl)-24-hydroxyl-5β-cholane (34). To a solution of free amine 32 (10 mg, 13 μmol) in 10 mL DMF was added N-methoxycarbonylmaleimide (20 mg, 0.13 mmol), and 1.0 mL Et$_3$N was added dropwise to the reaction mixture with stirring at room temperature. After stirring for 6 hours, the mixture was diluted with 20 mL ethyl acetate and washed with H$_2$O (2×20 mL) and brine. The organic layer was dried over anhydrous Na$_2$SO$_4$. The solvent was removed under vacuum and the residue was purified through flash chromatography with elution of ethyl acetate/hexane (5:95) to yield 34 as a light yellow oil (10 mg, 78%). $^1$H NMR (500 MHz, CDCl$_3$/TMS) δ 6.73 (s, 6H, OCHC=CH), 3.79 (d, 2H, J=2.5 Hz, H$_2$—C(24)), 3.74 (m, 6H, CH$_2$CH$_2$NCO), 3.68-3.57 (m, 6H, OCH$_2$CCH$_2$CH$_2$S), 3.57-3.42 (m, 6H, SCH$_2$CH$_2$N), 3.22 (b, 1H, HO—C(24)), 3.20 (m, 1H, H—C(12)), 3.17 (m, 1H, H—C(7)), 3.05 (m, 1H, H—C(3)), 2.72 (m, 6H, OCH$_2$CH$_2$CH$_2$S,), 2.69-2.60 (m, 6H, OCH$_2$CH$_2$CH$_2$S), 2.15-0.98 (series of multiplet, 24H), 0.92 (d, 3H, J=6.5 Hz, H$_3$C—C(20)), 0.88 (s, 3H, H$_3$C—C(10)), 0.65 (s, 3H, H$_3$C—C(13)); $^{13}$C NMR (500 MHz, CDCl$_3$/TMS) 187.05, 176.13, 170.73, 166.02, 160.98, 157.37, 156.08, 155.85, 134.12, 134.27, 134.30, 134.36, 135.06, 136.6, 104.75 ,99.57, 90.05, 60.01, 57.73, 50.85, 49.9, 48.23, 37.06, 37.02, 37.10, 36.13, 29.14; 29.10, 29.00. ESI-MS calcd. for C$_{51}$H$_{76}$N$_3$O$_{10}$S$_3$$^+$ (M+H)$^+$: 986.46; found: 986.84 (M+H)$^+$, 771.73 (M−215+H)$^+$, 556.59. (M−2×215+H)$^+$.

3α, 7α, 12α-tri-[6-(2-Bromoacetylamido-3-thia-hexyoxyl)]-24-hydroxyl-5β-cholane (35). Method A: to a solution of free amine 32 (12 mg, 16 μmol) in 10 mL DCM was added Bromoacetic anhydride (17 mg, 64 μmol). The mixture was stirred at room temperature for 3 hour; TLC showed no more free amine remained in the reaction mixture. The solvent was removed under vacuum, the residue was purified through flash chromatography with elution of ethyl acetate/hexane (60:40) to give 35 as a pale white oil (16 mg, 89%).

Method B: amine 32 (12 mg, 16 μol) was dissolved in 10 mL mixture of MeCN/0.5 M NaHCO$_3$ (50:50), Bromoacetic anhydride (25 mg, 96 μmol) was added. The mixture was stirred for 2 hours, worked-up of the reaction mixture was in the same way as in method A to give 35 (17 mg, 96%).

$^1$H NMR (500 MHz, CDCl$_3$/TMS) of 35: δ 4.04 (m, 1H, H—C(24)), 4.00 (m, 1H, H—C(24)), 3.93 (m, 6H, OCH$_2$CCH$_2$CH$_2$S), 3.89 (m, 6H, CH$_2$CH$_2$NH), 3.61 (m, 6H, OCH$_2$CH$_2$CH$_2$S), 3.32 (m, 1H, H—C(12)), 3.25 (b, 1H, HO—C(24)), 3.14 (m, 7H, NCH$_2$CH$_2$S, H—C(7)), 3.08 (m, 1H, H—C(3)), 2.71 (m, 3H, OCH$_2$CHHCH$_2$S), 2.63 (m, 3H, OCH$_2$CHHCH$_2$S), 2.20-1.05 (series of multiplet, 32H), 1.82 (bs, 6H, OCCH$_2$Br), 0.92 (d, 3H, J=6.0 Hz, H$_3$C—C(20)), 0.89 (s, 3H, H$_3$C—C(10)), 0.66 (s, 3H, H$_3$C—C(13)); $^{13}$C NMR (500 MHz, CDCl$_3$/TMS) 80.82, 79.95, 76.15, 66.19, 65.82, 62.47, 46.52, 46.29, 42.86, 42.10, 40.64, 39.87, 38.91, 38.86, 35.72, 35.45, 35.12, 34.82, 32.11, 30.14, 29.93, 29.83, 28.93, 28.79, 28.61, 28.54, 28.47, 28.33, 28.00, 27.65, 27.59, 27.34, 25.60, 23.32, 22.72, 22.16, 17.52, 17.13, 14.47, 13.55, 11.75; ESI-MS calcd. for C$_{45}$H$_{79}$Br$_3$N$_3$O$_7$S$_3$$^+$ (M+H)$^+$: 1110.26; found: 1110.52 (M+H)$^+$, 555.58 (M+2H)$^{2+}$.

General method for the ligation of thiol-containing peptides to the cholic acid-based maleimide clusters. The peptides (4.5-5.0 equivalent of maleimide) were dissolved in degassed phosphate buffer (pH 6.6)/acetonitrile (1:1), maleimide 33 or 34 dissolved in acetonitrile was added. The concentration was controlled of 2 μmol/mL approximately. The mixture was gently shaking constantly. The processing of ligation was monitored with analytic HPLC in a proper interval of time until starting peptides were consumed mostly. The mixture of reaction was purified with RP-HPLC. The collected desired fraction was lyophilized, and white cotton-like solid was obtained. The purity of the products was confirmed by HPLC and the identities were characterized by ESI-MS.

Trivalent peptide (36a) 83% yield; Retention time ($t_R$) 19.03 min (0.1% TFA MeCN/H$_2$O 0 to 90%); ESI-MS: 1889.74 (M+8H)$^{8+}$, 1680.20 (M+9H)$^{9+}$, 1512.32 (M+10H)$^{10+}$, 1374.92 (M+11H)$^{11+}$, 1260.44 (M+12H)$^{12+}$, 1163.64 (M+13H)$^{13+}$, 1080.46 (M+14H)$^{14+}$.

Trivalent peptide (36b) 91% yield; $t_R$ 19.03 min (0.1% TFA MeCN/H$_2$O 0 to 90%); ESI-MS: 155.33 (M+5H)$^{5+}$, 1294.71 (M+6H)$^{6+}$, 1109.88 (M+7H)$^{7+}$, 971.31 (M+8H)$^{8+}$, 863.56 (M+9H)$^{9+}$.

Trivalent peptide (37a) 90% yield; $t_R$ 12.69 min (0.1% TFA MeCN/H$_2$O 0 to 90%); ESI-MS: 1852.35 (M+2H)$^{2+}$, 1235.16 (M+3H)$^{3+}$, 926.63 (M+4H)$^{4+}$, 752.58 (M+5H)$^{5+}$.

Trivalent peptide (37b) 82% yield; $t_R$ 13.59 min (0.1% TFA MeCN/H$_2$O 0 to 90%); ESI-MS: 1847.83 (M+8H)$^{8+}$, 1642.74 (M+9H)$^{9+}$, 1478.59 (M+10H)$^{10+}$, 1344.26 (M+11H)$^{11+}$, 1232.32 (M+12H)$^{12+}$, 1137.72 (M+13H)$^{13+}$, 1056.34 (M+14H$^{14+}$.

Trivalent peptide (37c) 20% yield; $t_R$ 16.60 min (0.1% TFA MeCN/H$_2$O 0 to 90%); ESI-MS: 1485.67 (M+5H)$^{5+}$, 1238.18 (M+6H)$^{6+}$, 1061.51 (M+7H)$^{7+}$, 928.94 (M+8H)$^{8+}$, 825.98 (M+9H)$^{9+}$.

Trivalent peptide (38). Ligation of peptide and the bromoacetyl derivative. The peptide P-7C (9.7 mg, 11 μmol) was dissolved in degassed 3 mL sodium borate buffer (pH 8.5)/acetonitrile (1:1) mixture. Bromoacetyl derivative 35 (2.6 mg, 2.4 μmol) dissolved in the acetonitrile was added with gentle shaking. The processing of ligation was monitored with analytic HPLC in a proper interval of time until starting peptide was consumed mostly. The mixture of reaction was purified with RP-HPLC, the collected fraction of 38 was lyophilized to provide as a white cotton-like solid (3 mg, 35%). $t_R$ 12.26 min (0.1% TFA MeCN/H$_2$O 0 to 90%); ESI-MS: 1792.26 (M+2H)$^{2+}$, 1195.14 (M+3H)$^{3+}$, 896.74 (M+4H)$^{4+}$, 717.68 (M+5H)$^{5+}$.

Circular Dichroism (CD)

The samples of tetravalent peptide 26, trivalent peptides 36a and 37b, template 3α, 7α, 12α-tri-(6-Amino-3-thiahexy-oxyl)-24-hydroxyl-5β-cholane 32, and the single peptide DP178 were prepared in a concentration ranging from 2 to 18 μM in 50 mM phosphate buffer (pH 7.4). The exact concentration of each sample was detected by UV spectrometer just prior to CD measurement. The measurement was run at 25° C. Blank was subtracted from the CD spectra, which were the average of three times scans.

The prior disclosure and examples are provided as illustration of the disclosed invention and are not intended to limit the scope of the invention.

REFERENCES

All cited references are herein incorporated in their entirety by reference.

1. Akerfeldt, K. S., R. M. Kim, D. Camac, J. T. Groves, J. D. Lear, and W. F. DeGrade. 1992. Tetraphilin: a four-helix proton channel built on a tetraphenylporphyrin framework. J. Am. Chem. Soc. 114:9656-9657.
2. Blaskovich, M. A., Q. Lin, F. L. Delarue, J. Sun, H. S. Park, D. Coppola, A. D. Hamilton, and S. M. Sebti. 2000. Design of GFB-111, a platelet-derived growth factor binding molecule with antiangiogenic and anticancer activity against human tumors in mice. Nat. Biotechnol. 18:1065-70.
3. Brask, J., and K. J. Jensen. 2000. Carbopeptides: chemoselective ligation of peptide aldehydes to an aminooxy-functionalized D-galactose template. J. Pept. Sci. 6:290-9.
4. Brask, J., and K. J. Jensen. 2001. Carboproteins: a 4-alpha-helix bundle protein model assembled on a D-galactopyranoside template. Bioorg. Med. Chem. Lett. 11:697-700.
5. Calyo-Calle, J. M., G. A. de Oliveira, P. Clavijo, M. Maracic, J. P. Tam, Y. A. Lu, E. H. Nardin, R. S. Nussenzweig, and A. H. Cochrane. 1993. Immunogenicity of multiple antigen peptides containing B and non-repeat T cell epitopes of the circumsporozoite protein of Plasmodium falciparum. J. Immunol. 150:1403-12.
6. Chan, D. C., and P. S. Kim. 1998. HIV entry and its inhibition. Cell. 93:681-4.
7. Dubber, M., and T. K. Lindhorst. 1998. Synthesis of octopus glycosides: core molecules for the construction of glycoclusters and carbohydrate-centered dendrimers. Carbohydr. Res. 310:35-41.
8. Guan, Q.; Li, C.; Schmidt, E. J.; Boswell, J. S.; Walsh, J. P.; Allman, G. W.; Savage, P. B. 2000. Preparation and Characterization of Cholic Acid-Derived Antimicrobial Agents with Controlled Stabilities. Org. Lett. 2:2837-2840.
9. Jensen, K. J., and G. Barany. 2000. Carbopeptides: carbohydrates as potential templates for de novo design of protein models. J. Pept. Res. 56:3-11.
10. Kilby, J. M., S. Hopkins, T. M. Venetta, B. DiMassimo, G. A. Cloud, J. Y. Lee, L. Alldredge, E. Hunter, D. Lambert, D. Bolognesi, T. Matthews, M. R. Johnson, M. A. Nowak, G. M. Shaw, and M. S. Saag. 1998. Potent suppression of HIV-1 replication in humans by T-20, a peptide inhibitor of gp41-mediated virus entry. Nat. Med. 4:1302-7.
11. Kitagawa, T., and T. Aikawa. 1976. Enzyme coupled immunoassay of insulin using a novel coupling reagent. J. Biochem. (Tokyo). 79:233-6.
12. Lawless, M. K., S. Barney, K. I. Guthrie, T. B. Bucy, S. R. Petteway, Jr., and G. Merutka. 1996. HIV-1 membrane fusion mechanism: structural studies of the interactions between biologically-active peptides from gp41. Biochemistry. 35:13697-708.
13. Leydet, A., C. Jeantet-Segonds, C. Bouchitte, C. Moullet, B. Boyer, J. P. Roque, M. Witvrouw, J. Este, R. Snoeck, G. Andrei, and E. De Clercq. 1997. Polyanion inhibitors of human immunodeficiency virus and other viruses. 6. Micelle-like anti-HIV polyanionic compounds based on a carbohydrate core. J. Med. Chem. 40:350-6.
14. Lin, Q., H. S. Park, Y. Hamuro, C. S. Lee, and A. D. Hamilton. 1998. Protein surface recognition by synthetic agents: design and structural requirements of a family of artificial receptors that bind to cytochrome c. Biopolymers. 47:285-97.
15. Lindhorst, T. K. 2002. Artificial multivalent sugar ligands to understand and manipulate carbohydrate-protein interactions. Top. Curr. Chem. 218:201-235.
16. Lu, Y. A., P. Clavijo, M. Galantino, Z. Y. Shen, W. Liu, and J. P. Tam. 1991. Chemically unambiguous peptide immunogen: preparation, orientation and antigenicity of purified peptide conjugated to the multiple antigen peptide system. Mol. Immmmol. 28:623-30.
17. Lyu, P. C.; Sherman, J. C.; Chen, A.; Kallenbach, N. R. 1991. a-Helix stabilization by natural and unnatural amino acids with alkyl side chains. Proc. Natl. Acad. Sci. USA. 88:5317-5320.
18. Madder, A.; Li, L.; De Muynck, H.; Farcy, N.; Van Haver, D.; Fant, F.; Vanhoenacker, G.; Sandra, P.; Davis, A. P.; De Clercq, P. J. 2002. Evaluation of a Two-Stage Screening Procedure in the Combinatorial Search for Serine Protease-Like Activity. J. Comb. Chem. 4:552-562.
19. Malashkevich, V. N., D. C. Chan, C. T. Chutkowski, and P. S. Kim. 1998. Crystal structure of the simian immunodeficiency virus (SIV) gp41 core: conserved helical interactions underlie the broad inhibitory activity of gp41 peptides. Proc. Natl. Acad. Sci. USA. 95:9134-9.
20. McGeary, R. P., I. Jablonkai, and I. Toth. 2001. Carbohydrate-based templates for synthetic vaccines and drug delivery. Tetrahedron. 57:8733-8742.
21. Muster, T., F. Steindl, M. Purtscher, A. Trkola, A. Klima, G. Himmler, F. Ruker, and H. Katinger. 1993. A conserved neutralizing epitope on gp41 of human immunodeficiency virus type 1. J. Virol. 67:6642-7.
22. Mutter, M., and G. Tuchscherer. 1997. Non-native architectures in protein design and mimicry. Cell Mol. Life Sci, 53:851-63.
23. Mutter, M., G. G. Tuchscherer, C. Miller, K. H. Altmann, R. I. Carey, D. F. Wyss, A. M. Labhardt, and J. Rivier. 1992. Template-assembled synthetic proteins with four-helix-bundle topology. Total chemical and conformational studies. J. Am. Chem. Soc. 114:1463-1470.
24. Nardelli, B., Y. A. Lu, D. R. Shiu, C. Delpierre-Defoort, A. T. Profy, and J. P. Tam. 1992. A chemically defined synthetic vaccine model for HIV-1. J. Immunol. 148:914-20.
25. Nefzi, A.; Sun, X.; Mutter, M. 1995. Chemoselective ligation of multifunctional peptides to topological templates via thioether formation for TASP synthesis. Tetrahedron Lett. 36:229-230.
26. Ni, J., S. Singh, and L. X. Wang. 2002. Improved preparation of perallylated cyclodextrins: facile synthesis of cyclodextrin-based polycationic and polyanionic compounds. Carbohydr Res. 337:217-20.
27. Park, H. S., Q. Lin, and A. D. Hamilton. 1999. Protein surface recognition by synthetic receptors: a route to novel submicromolar inhibitors for alpha-chymotrypsin. J. Am. Chem. Soc. 121:8-13.
28. Peczuh, M. W., and A. D. Hamilton. 2000. Peptide and protein recognition by designed molecules. Chem. Rev. 100:2479-2494.
29. Peeters, J. M., T. G. Hazendonk, E. C. Beuvery, and G. I. Tesser. 1989. Comparison of four bifunctional reagents for coupling peptides to proteins and the effect of the three moieties on the immunogenicity of the conjugates. J. Immunol. Methods. 120:133-43.
30. Robey, F. A., and R. L. Fields. 1989. Automated synthesis of N-bromoacetyl-modified peptides for the preparation of synthetic peptide polymers, peptide-protein conjugates, and cyclic peptides. Anal. Biochem. 177:373-7.
31. Rose, K. 1994. Facile synthesis of homogeneous artificial proteins. J. Am. Chem. Soc. 116:30-33.
32. Roy, T. 1997. Rational developments in the rational design of multivalent glycoconjugates. Top. Curr. Chem. 187:241-274.
33. Sasaki, T., and E. T. Kaiser. 1989. Helichrome: Synthesis and enzymatic activity of a designed hemeprotein. J. Am. Chem. Soc. 111:380-381.
34. Shao, J., and J. P. Tam. 1995. Unprotected peptides as building blocks for the synthesis of peptide dendrimers with oxime, hydrazone, and thiazolidine linkages. J. Am. Chem. Soc. 117:3893-3899.
35. Tam, J. P. 1996. Recent advances in multiple antigen peptides. J. Immunol. Methods. 196:17-32.
36. Tam, J. P. 1988. Synthetic peptide vaccine design: synthesis and properties of a high-density multiple antigenic peptide system. Proc. Natl. Acad. Sci. USA. 85:5409-13.
37. Tam, J. P., and Y. A. Lu. 1989. Vaccine engineering: enhancement of immunogenicity of synthetic peptide vaccines related to hepatitis in chemically defined models consisting of T- and B-cell epitopes. Proc. Natl. Acad. Sci. USA. 86:9084-8.
38. Tam, J. P., Y. A. Lu, and J. L. Yang. 2002. Antimicrobial dendrimeric peptides. Eur. J. Biochem. 269:923-932.
39. Tuchscherer, G. 1993. Template assembled synthetic proteins: condensation of a multifunctional peptide to a topological template via chemoselective ligation. Tetrahedron Lett. 34:8419-8422.
40. Tuchscherer, G., D. Grell, M. Mathieu, and M. Mutter. 1999. Extending the concept of template-assembled synthetic proteins. J. Pept. Res. 54:185-94.
41. Tuchscherer, G., C. Servis, G. Corradin, U. Blum, J. Rivier, and M. Mutter. 1992. Total chemical synthesis, characterization, and immunological properties of an MHC class I model using the TASP concept for protein de novo design. Protein Sci. 1:1377-86.
42. Wang, C. Y., D. J. Looney, M. L. Li, A. M. Walfield, J. Ye, B. Hosein, J. P. Tam, and F. Wong-Staal. 1991. Long-term high-titer neutralizing activity induced by octameric synthetic HIV-1 antigen. Science. 254:285-8.
43. Wang, L. X.; Ni, J.; Singh, S. 2003. Carbohydrate-centered maleimide cluster as a new type of templates for multivalent peptide assembling: Synthesis of multivalent HIV-1 gp41 peptides. Bioorg. Med. Chem., 11:159-166.
44. Wild, C., T. Greenwell, and T. Matthews. 1993. A synthetic peptide from HIV-1 gp41 is a potent inhibitor of virus-mediated cell-cell fusion. AIDS Res. Hum. Retroviruses. 9:1051-3.
45. Wild, C. T., D. C. Shugars, T. K. Greenwell, C. B. McDanal, and T. J. Matthews. 1994. Peptides corresponding to a predictive alpha-helical domain of human immunodeficiency virus type 1 gp41 are potent inhibitors of virus infection. Proc. Natl. Acad. Sci. USA. 91:9770-4.
46. Zhou, X.-T.; Atiq-ur-Rehman; Li, C.; Savage, P. B. 2000. Preparation of a Protected Triamino Analogue of Cholic Acid and Sequential Incorporation of Amino Acids in Solution and on a Solid Support. Org. Lett. 2:3015-3018.

We claim:

1. A maleimide cluster comprising a core carbohydrate molecule wherein the core is selected from the group consisting of monosaccharides, oligosaccharides, and cyclic oligosaccharides and wherein at least two or more maleimide containing groups are attached to the core, wherein the maleimide containing groups are linked to the carbohydrate core by an alkyl cysteamine linker and optionally comprising a protein is covalently attached to the maleimide.

2. The maleimide cluster according to claim 1, wherein the core carbohydrate molecule is a monosaccharide.

3. The maleimide cluster according to claim 2 wherein four or more maleimide containing groups are attached to the core by the linker.

4. The maleimide cluster according to claim 1, wherein the core comprises cyclodextrin and wherein one or more maleimide containing groups are each attached to the cyclodextrin.

5. The maleimide cluster of claim 2 further comprising a protein covalently attached to each of the maleimide containing groups, wherein proteins attached to the maleimide containing groups have the same or different amino acid sequences.

6. A method of delivering a peptide drug comprising administering a multivalent peptide containing a therapeutically effective amount of the peptide drug to a patient in need thereof, wherein the multivalent peptide comprises peptides covalently attached to the maleimide cluster of claim 2.

7. The method of claim 6, wherein the covalently attached peptides comprise the same or different amino acid sequences.

8. A method of making a multivalent protein comprising contacting proteins containing a thiol group with the maleimide cluster according to claim 2 and forming a covalent bond thereto.

9. The method of claim 8, wherein the covalently bonded proteins the same or different amino acid sequences.

10. The maleimide cluster according to claim 2 comprising a protein covalently attached to each maleimide containing groups, wherein the protein is an HIV antigen.

* * * * *

SEQUENCE LISTING

<160> NUMBER OF SEQ ID NOS: 5

<210> SEQ ID NO 1
<211> LENGTH: 7
<212> TYPE: PRT
<213> ORGANISM: Artificial Sequence
<220> FEATURE:

```
<223> OTHER INFORMATION: Synthetic Construct

<400> SEQUENCE: 1

Glu Leu Asp Lys Trp Ala Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Cys Glu Leu Asp Lys Trp Ala
1               5

<210> SEQ ID NO 3
<211> LENGTH: 37
<212> TYPE: PRT
<213> ORGANISM: Artificial Sequence
<220> FEATURE:
<223> OTHER INFORMATION: Synthetic Construct

<400> SEQUENCE: 3

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Cys
        35

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Glu Leu Asp Lys Trp Ala
1               5

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct

<400> SEQUENCE: 5

Cys Gly Ser Ser Ser Gln Tyr Ile Lys Ala Asn Ser Lys Phe Ile Gly
1               5                   10                  15

Ile Thr Glu Leu
            20
```